US009592244B2

(12) United States Patent
Angi et al.

(10) Patent No.: US 9,592,244 B2
(45) Date of Patent: Mar. 14, 2017

(54) COMPLEXES OF ABIRATERONE ACETATE, PROCESS FOR THE PREPARATION THEREOF AND PHARMACEUTICAL COMPOSITIONS CONTAINING THEM

(71) Applicant: Druggability Technologies IP Holdco Limited, Swatar (MT)

(72) Inventors: Erzsébet Réka Angi, Nagykovácsi (HU); Tamás Jordán, Öcsöd (HU); Orsolya Basa-Dénes, Eger (HU); Tamás Solymosi, Békéscsaba (HU); Zsolt Ötvös, Csongrád (HU); Hristos Glavinas, Szeged (HU); Genovéva Filipcsei, Budapest (HU)

(73) Assignee: Druggability Technologies IP Holdco Limited, Swatar (MT)

( * ) Notice: Subject to any disclaimer, the term of this patent is extended or adjusted under 35 U.S.C. 154(b) by 0 days.

(21) Appl. No.: 15/222,301

(22) Filed: Jul. 28, 2016

(65) Prior Publication Data

US 2016/0331763 A1 Nov. 17, 2016

Related U.S. Application Data

(62) Division of application No. 15/019,037, filed on Feb. 9, 2016.

(30) Foreign Application Priority Data

Feb. 9, 2015 (HU) ..................................... 1500055

(51) Int. Cl.
*A61K 31/58* (2006.01)
*A61K 47/48* (2006.01)
*A61K 9/19* (2006.01)
*A61K 9/16* (2006.01)
*A61K 9/51* (2006.01)

(52) U.S. Cl.
CPC ............ *A61K 31/58* (2013.01); *A61K 9/1617* (2013.01); *A61K 9/1641* (2013.01); *A61K 9/1682* (2013.01); *A61K 9/1694* (2013.01); *A61K 9/19* (2013.01); *A61K 9/5123* (2013.01); *A61K 9/5138* (2013.01); *A61K 47/48176* (2013.01); *A61K 47/48215* (2013.01)

(58) Field of Classification Search
CPC ..... A61K 31/58; A61K 9/19; A61K 47/48176
See application file for complete search history.

(56) References Cited

U.S. PATENT DOCUMENTS

| 5,604,213 | A | 2/1997 | Barrie et al. |
| 5,688,977 | A | 11/1997 | Sisti et al. |
| 8,822,438 | B2 | 9/2014 | Auerbach et al. |
| 2010/0022680 | A1* | 1/2010 | Karnik .................. B82Y 30/00 523/105 |
| 2015/0133416 | A1* | 5/2015 | Grenier .................. A61K 9/145 514/176 |

FOREIGN PATENT DOCUMENTS

WO 2013164473 A1 * 5/2013

OTHER PUBLICATIONS

Armstrong A. et al., New drugs in prostate cancer, Curr Opin Urol 16, 138-145, 2006.
Attard, G. et al., Selective blockade of androgenic steroid synthesis by novel lyase inhibitors as a therapeutic strategy for treating metastatic prostate cancer, Br J Urol 96(9), 1241-1246, 2005.
Attard, G. et al., Phase I Clinical Trial of a Selective Inhibitor of CYP17, Abiraterone Acetate, Confirms That Castration-Resistant Prostate Cancer Commonly Remains Hormone Driven, J Clin Oncol 26(28), 4563-4571, 2008.
Attard, G. et al., Selective Inhibition of CYP17 With Abiraterone Acetate Is Highly Active in the Treatment of Castration-Resistant Prostate Cancer, J Clin Oncol 27(23), 3742-3748, 2009.
Auchus, R., The genetics, pathophysiology, and management of human deficiencies of P450c17, Endocrinol Metab Clin North Am 30(1), 101-119, 2001.
Boehringer-Ingelheim and British Technology Group Press Release—New Treatment for Prostate Cancer Under Development, dated May 22, 1996, 1 page.
Boumpas, D. et al., Glucocorticoid Therapy for Immune-mediated Diseases: Basic and Clinical Correlates, Ann Internal Med 119, 1198-1208, 1993.
Burgess, E. et al., Changing Perspectives of the Role of Chemotherapy in Advanced Prostate Cancer, Urol Clin N Am 33, 227-236, 2006.
Cancer.net (ASCO Patient Website), Treatment of Metastatic Castration-Resistant Prostate Cancer, http://www.cancer.net/research-and-advocacy/asco-careand-treatment-recommendations-patients/treatment-metastatic-castrationresistant-prostate-cancer, accessed Jul. 24, 2015, 3 pages.
Cancer.org (ACS), What are the key statistics about prostate cancer? http://www.cancer.org/cancer/prostatecancer/detailed guide/prostatecancerkeystatistics, accessed Aug. 20, 2015, 1 page.
Clinical Cancer Research Peer Review letter to Ian Judson, dated May 12, 2003, 4 pages.
Conde, F. et al., Risk factors for male osteoporosis, Urologic Oncology: Seminar and Original Investigations 21, 380-383, 2003.
Costa-Santos, M. et al., Two Prevalent CYP17 Mutations and Genotype-Phenotype Correlations in 24 Brazilian Patients with 17-Hydroxylase Deficiency, J Clin Endocrin & Metabol 89(1), 49-60, 2004.

(Continued)

*Primary Examiner* — Yanzhi Zhang
(74) *Attorney, Agent, or Firm* — Dennis A. Bennett

(57) ABSTRACT

The present disclosure relates to pharmaceutically acceptable complex formulae comprising complexes of Abiraterone acetate and pharmaceutically acceptable excipients, process for the preparation thereof and pharmaceutical compositions containing them. The complex formulae of the present disclosure have improved physicochemical properties which results in reduced food effect which allows significant dose reduction and the abandoning of the requirement of taking the drug on an empty stomach.

6 Claims, 20 Drawing Sheets

(56) References Cited

OTHER PUBLICATIONS

Cowen & Company, Biotechnology Quarterly, Jul. 2, 2012, pp. 612, 1006-1009.

Cowen & Company, Johnson & Johnson, Quick Take: Zytiga Gets FDA OK for Use in Pre-Chemo Setting on rPFS Data, Dec. 11, 2012, 3 pages.

Credit Suisse, Prostate Cancer—Implications of Zytiga's Pre-Chemo Approval, Dec. 11, 2012, 7 pages.

Danila, D. et al., Phase II Multicenter Study of Abiraterone Acetate Plus Prednisone Therapy in Patients With Docetaxel-Treated Castration-Resistant Prostate Cancer, J Clin Oncol 28(9), 1496-1501, 2010.

de Bono, J. et al., Abiraterone and Increased Survival in Metastatic Prostate Cancer, N Engl J Med 364(21), 1995-2005, 2011.

Debruyne, F. et al., Ketoconazole High Dose (H.D.) In the Management of Metastatic Prostatic Carcinoma, Journal of Urology 135(4, pt.2), 203A, Abstract 397, 1986.

Declaration of Dr. DeForest McDuff, PhD, dated Dec. 4, 2015, 56 pages.

Declaration of Dr. Scott Serels, MD, dated Dec. 4, 2015, 46 pages.

Declaration of Professor Ian Judson, dated Jun. 29, 2015, 3 pages.

Duc, I. et al., In vitro and in vivo models for the evaluation of potent inhibitors of male rat 17α-hydroxylase/$C_{17,20}$-lyase, Journal of Steroid Biochemistry & Molecular Biology 84, 537-542, 2003.

FDA News Release, FDA Approves New Indication for Taxotere-Prostate Cancer, May 19, 2004, 2 pages.

FDA News Release, FDA expands Zytiga's use for late-stage prostate cancer, Dec. 10, 2012, http://www.fda.gov/NewsEvents/Newsroom/PressAnnouncements/ucm331492.htm, 3 pages.

FDA Website, Drugs@FDA—Zytiga, http://www.accessdata.fda.gov/scripts/cder/drugsatfda/index.cfm?fuseaction=Search. DrugDetails, accessed Jul. 23, 2015, 2 pages.

FDA Website, Orange Book, Zytiga (NDA 202379), http://www.accessdata.fda.gov/scripts/cder/ob/docs/patexclnew.cfm?Appl_No=202379&Product_No=001&table1=OB_Rx, accessed Jul. 24, 2015, 2 pages.

*Galderma Laboratories, L.P. et al. v. Tolmar, Inc.*, 737 F.3d 731, 740-741 (Fed. Cir. 2013).

Gerber, G. et al., Prostate specific antigen for assessing response to ketoconazole and prednisone in patients with hormone refractory metastatic prostate cancer, J Urol 144(5),1177-1179, 1990.

Hadaschik, B. et al., Novel targets and approaches in advanced prostate cancer, Curr Opin Urol 17, 182-187, 2007.

Harris, K. et al., Low dose Ketoconazole with replacement doses of hydrocortisone in patients with progressive androgen independent prostate cancer, J Urol 168, 542-545, Aug. 2002.

Hellerstedt, B. et al., The Current State of Hormonal Therapy for Prostate Cancer, CA Cancer J Clin 52, 154-179, 2002.

Herr, I. et al., Glucocorticoid use in prostate cancer and other solid tumours: implications for effectiveness of cytotoxic treatment and metastases, Lancet Oncol 7, 425-430, 2006.

IMS Health Data 2012-2015 for Zytiga®, Xtandi® and Jevtana®, 1 page.

Jevtana® Website, Dosing and Administration, http://www.jevtana.com/hcp/dosing/default.aspx, accessed Aug. 20, 2015, 3 pages.

Jubelirer, S. et al, High Dose Ketoconazole for the Treatment of Hormone Refractory Metastatic Prostate Carcinoma: 16 Cases and Review of the Literature, J Urol 142, 89-91, 1989.

Kasper, D. et al. (Eds.), Harrison's Principles of Internal Medicine, 16th Edition (2005), p. 549.

Kirby, M. et al., Characterising the Castration-Resistant Prostate Cancer Population: A Systematic Review, Int J Clin Pract 65(11), 1180-1192, 2011.

Krishnan et al., A Glucocorticoid-Responsive Mutant Androgen Receptor Exhibits Unique Ligand Specificity: Therapeutic Implications for Androgen-Independent Prostate Cancer, Endocrinology 143(5), 1889-1900, 2002.

Mayo Clinic Website, Prostate cancer, http://www.mayoclinic.org/diseasesconditions/prostate-cancer/basics/definition/con-20029597?p=1, accessed Jul. 24, 2015, 12 pages.

Medivation Press Release, U.S. FDA Approves New Indication for the Use of Xtandi® (Enzalutamide) Capsules for Patients With Metastatic Castration-Resistant Prostate Cancer, Sep. 10, 2014, http://investors.medivation.com/releasedetail.cfm?ReleaseID=870267, 3 pages.

*Merck & Co., Inc. v. Teva Pharmaceuticals USA, Inc.*, 395 F.3d 1364, 1376-1377 (Fed. Cir. 2005).

Murphy, W. et al., Patent Valuation: Improving Decision Making through Analysis, Chapter 5: Preparing for the Valuation, 91-120, 2012.

O'Donnell, A. et al., Hormonal impact of the 17α-hydroxylase/$C_{17,20}$-lyase inhibitor abiraterone acetate (CB7630) in patients with prostate cancer, Br J of Cancer 90, 2317-2325, 2004.

Oh, W., Secondary hormonal therapies in the treatment of prostate cancer, Urology 60(Suppl 3A), 87-93, 2002.

Orange Book listing for Zytiga®, approved Apr. 28, 2011, 2 pages.

Papatsoris, A.G. et al., Novel Biological Agents for the Treatment of Hormone-Refractory Prostate Cancer (HRPC), Current Medicinal Chemistry 12, 277-296, 2005.

PMLiVE Website, Top 50 Pharmaceutical Products by Global Sales, http://www.pmlive.com/top_pharma_list/Top_50_pharmaceutical_products_by_global_sales, accessed Sep. 14, 2015, 2 pages.

Public Citizen Press Room Release—Antifungal Treatment Should Be Taken Off the Market, Public Citizen Tells FDA, dated Feb. 24, 2015, 1 page.

RBC Capital Markets (via Barron's Website), Xtandi Beats Casodex, Set to Top Zytiga, Apr. 3, 2015, http://online.barrons.com/articles/xtandi-beats-casodexset-to-top-zytiga-1428075331, accessed Jul. 24, 2015, 2 pages.

Remington: The Science and Practice of Pharmacy, 20th ed., 1363-1370, 2000.

Rumohr, J. et al., Current chemotherapeutic approaches for androgen-independent prostate cancer, Current Opinion in Investigational Drugs 7(6), 529-533, 2006.

Ryan, C. et al., Phase II Study of Abiraterone in Chemotherapy-Naive Metastatic Castration-Resistant Prostate Cancer Displaying Bone Flare Discordant with Serologic Response, Clin Cancer Res 17(14), 4854-4861, 2011.

Ryan, C. et al., Abiraterone in metastatic prostate cancer without previous chemotherapy, N Engl J Med 368, 138-148, 2012.

Scher, H. et al., Increased Survival with Enzalutamide in Prostate Cancer after Chemotherapy, N Eng J Med 367(13) 1187-1197, 2012.

Strother, J. et al., Novel cytotoxic and biological agents for prostate cancer: Where will the money be in 2005?, European Journal of Cancer 41, 954-964, 2005.

*Syntex (U.S.A.) LLC and Allergan, Inc. v. Apotex, Inc. et al.*, 407 F.3d 1371, 1383 (Fed. Cir. 2005).

Tannock, I. et al., Treatment of metastatic prostatic cancer with low-dose prednisone: evaluation of pain and quality of life as pragmatic indices of response, J Clin Oncol 7(5), 590-597, 1989.

Tannock et al., "Chemotherapy with mitoxantrone plus prednisone or prednisone alone for symptomatic hormone-resistant prostate cancer: a Canadian randomized trial with palliative end points," J Clin Oncol 14, 1756-1764, 1996.

Tannock, I. et al., Docetaxel plus Prednisone or Mitoxantrone plus Prednisone for Advanced Prostate Cancer, N Eng J Med 351, 1502-1512, 2004.

Taxotere® Prescribing Information, 2004, 35 pages.

UBS Investment Research, Johnson & Johnson—Zytiga Label extended, Dec. 10, 2012, 10 pages.

UBS Research, Medivation—A Look at the Growth and Share in Prostate Cancer, Feb. 3, 2014, 2 pages.

Wedbush Securities, Inc., Medivation: Zytiga Market Share Decline Accelerates From Last Quarter, Jul. 14, 2015, 1 page.

Wells Fargo Securities, LLC., Johnson & Johnson—JNJ: Xtandi Continued Lead Zytiga in Overall Share in May, Jun. 29, 2015, 8 pages.

William Blair, Biotechnology—Zytiga Fourth-Quarter Sales Imply Xtandi Strength, Jan. 22, 2013, 4 pages.

(56) References Cited

OTHER PUBLICATIONS

William Blair, Medivation, Inc.—Looking into Recent Weaknesses, Jul. 14, 2015, 3 pages.

Williams, G. et al., Objective Responses to Ketoconazole Therapy in Patients with Relapsed Progressive Prostatic Cancer, Br J Urol 58, 45-51, 1986.

Zytiga® Brochure, Putting Prednisone in Perspective, 2015, 13 pages.

Zytiga® Label, May 2015, 30 pages.

Zytiga® Website, How Zytiga® (abiraterone acetate) Works, https://www.zytiga.com/print/about-zytiga/how-zytiga-works, accessed Jul. 23, 2015, 4 pages.

Zytiga® Prescribing Information, 2011, 22 pages.

Zytiga® Prescribing Information, 2015, 9 pages.

* cited by examiner

Figure 1.

| Complexing Agent | Citric Acid | D-Mannitol | DSS | Kollicoat-IR | Lutrol F127 | NaOAc | NONE | Plur PE10500 | SDC | SDS |
|---|---|---|---|---|---|---|---|---|---|---|
| Gelucire 44/14 | - | - | - | - | - | - | - | - | - | - |
| Gelucire 50/13 | - | - | - | - | - | - | - | - | - | - |
| Klucell EF | + | - | - | - | - | - | - | + | - | + |
| Lutrol F127 | - | - | + | - | - | - | - | + | + | - |
| Luviskol VA64 | + | - | - | - | - | + | - | - | - | + |
| PEOX50 | - | - | - | - | - | - | - | - | + | - |
| PEOX500 | + | - | - | - | + | - | - | - | - | + |
| Plasdone K-12 | + | - | - | - | - | - | - | + | - | + |
| Plur PE10500 | + | - | + | - | + | - | - | + | + | - |
| Plur PE6800 | + | - | - | - | - | - | - | - | - | - |
| Pluronic F108 | - | - | - | - | + | - | - | - | - | - |
| PMAMVE | - | - | + | - | + | - | - | - | + | + |
| PVP 40 | - | - | - | - | - | - | - | - | - | - |
| PVP K90 | + | - | + | - | - | - | - | - | - | + |
| PVP10 | + | - | - | - | - | - | - | - | - | - |
| Soluplus | + | - | - | - | - | + | - | + | + | + |
| Tetronic 1107 | + | - | + | - | - | - | + | - | - | - |
| TPGS | + | - | + | - | - | - | - | - | + | - |

COMPLEXES OF ABIRATERONE ACETATE, PROCESS FOR THE PREPARATION THEREOF AND PHARMACEUTICAL COMPOSITIONS CONTAINING THEM

This application is a divisional application claiming priority to U.S. patent application Ser. No. 15/019,037, filed Feb. 9, 2016, which itself claims the benefit of priority to application no. HU P1500055, filed Feb. 9, 2015, the disclosures of which are hereby incorporated by reference as if written herein in their entireties.

FIELD OF THE INVENTION

The disclosure is directed to a stable complex with controlled particle size, increased apparent solubility and increased dissolution rate comprising as active compound Abiraterone acetate, which is useful in the treatment of a certain type of prostate cancer that has spread to other parts of the body. Abiraterone acetate might be used for earlier stages of prostate cancer and advanced breast cancer. More specifically, the complex of the present disclosure possesses increased apparent solubility and exhibits no positive food effect which allows significant dose reduction and the abandoning of the requirement of taking the drug on an empty stomach. The disclosure also relates to methods of formulating and manufacturing complex according to the disclosure, pharmaceutical compositions containing it, its uses and methods of treatment using the complex and its compositions.

BACKGROUND OF THE INVENTION

Abiraterone is a potent and selective inhibitor of CYP17 (17α-hydroxylase/C17,20-lyase). As Abiraterone was poorly bioavailable and also susceptible to hydrolysis by esterases, a prodrug was developed. Abiraterone acetate (A) was found to be resistant to esterases and was rapidly deacetylated to Abiraterone (B) in vivo, resulting in potent CYP17 inhibition. Abiraterone acetate is designated chemically as (3β)-17-(3-pyridinyl) androsta-5,16-dien-3-yl acetate and its structure is:

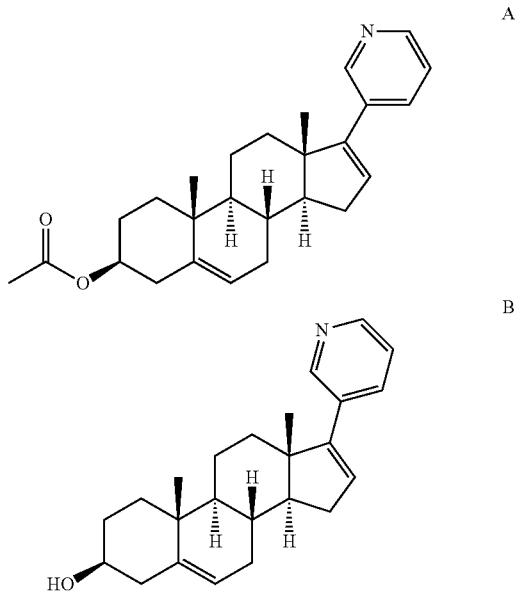

Abiraterone acetate is a white to off-white, non-hygroscopic, crystalline powder. Its molecular formula is $C_{26}H_{33}NO_2$ and it has a molecular weight of 391.55. Abiraterone acetate is a lipophilic compound with an octanol-water partition coefficient of 5.12 (Log P) and is practically insoluble in water. The pKa of the aromatic nitrogen is 5.19.

Inactive ingredients in the Zytiga® tablets are colloidal silicon dioxide, croscarmellose sodium, lactose monohydrate, magnesium stearate, microcrystalline cellulose, povidone, and sodium lauryl sulfate). Each Zytiga® tablet contains 250 mg of Abiraterone acetate.

Abiraterone acetate (ZYTIGA) is converted in vivo to Abiraterone, an androgen biosynthesis inhibitor, that inhibits 17α-hydroxylase/C17,20-lyase (CYP17). This enzyme is expressed in testicular, adrenal, and prostatic tumor tissues and is required for androgen biosynthesis.

CYP17 catalyzes two sequential reactions: 1) the conversion of pregnenolone and progesterone to their 17α-hydroxy derivatives by 17α-hydroxylase activity and 2) the subsequent formation of dehydroepiandrosterone (DHEA) and androstenedione, respectively, by C17,20 lyase activity. DHEA and androstenedione are androgens and are precursors of testosterone Inhibition of CYP17 by Abiraterone can also result in increased mineralocorticoid production by the adrenals.

Androgen sensitive prostatic carcinoma responds to treatment that decreases androgen levels. Androgen deprivation therapies, such as treatment with GnRH agonists or orchiectomy, decrease androgen production in the testes but do not affect androgen production by the adrenals or in the tumor.

Abiraterone acetate decreased serum testosterone and other androgens in patients in the placebo-controlled phase 3 clinical trial. It is not necessary to monitor the effect of Abiraterone on serum testosterone levels.

Changes in serum prostate specific antigen (PSA) levels may be observed but have not been shown to correlate with clinical benefit in individual patients.

Following administration of Abiraterone acetate, the pharmacokinetics of Abiraterone and Abiraterone acetate have been studied in healthy subjects and in patients with metastatic castration-resistant prostate cancer (CRPC). In vivo, Abiraterone acetate is converted to Abiraterone. In clinical studies, Abiraterone acetate plasma concentrations were below detectable levels (<0.2 ng/mL) in >99% of the analyzed samples.

Following oral administration of Abiraterone acetate to patients with metastatic CRPC, the median time to reach maximum plasma Abiraterone concentrations is 2 hours. Abiraterone accumulation is observed at steady-state, with a 2-fold higher exposure (steady-state AUC) compared to a single 1,000 mg dose of Abiraterone acetate.

At the dose of 1,000 mg daily in patients with metastatic CRPC, steady-state values (mean±SD) of $C_{max}$ were 226±178 ng/mL and of AUC were 993±639 ng*hr/mL. No major deviation from dose proportionality was observed in the dose range of 250 mg to 1,000 mg. However, the exposure was not significantly increased when the dose was doubled from 1,000 to 2,000 mg (8% increase in the mean AUC).

Systemic exposure of Abiraterone is increased when Abiraterone acetate is administered with food. Abiraterone $C_{max}$ and $AUC_{0-\infty}$ were approximately 7-and 5-fold higher, respectively, when Abiraterone acetate was administered with a low-fat meal (7% fat, 300 calories) and approximately 17-and 10-fold higher, respectively, when Abiraterone acetate was administered with a high-fat (57% fat, 825 calories) meal. Given the normal variation in the content and composition of meals, taking Zytiga® with meals has the potential to result in increased and highly variable exposures. Therefore, no food should be consumed for at least two hours before the dose of Zytiga® is taken and for at least one hour after the dose of Zytiga® is taken. The tablets should be swallowed whole with water.

Abiraterone is highly bound (>99%) to the human plasma proteins, albumin and alpha-1 acid glycoprotein. The apparent steady-state volume of distribution (mean±SD) is 19,669±13,358 L. In vitro studies show that at clinically relevant concentrations, Abiraterone acetate and Abiraterone are not substrates of P-glycoprotein (P-gp) and that Abiraterone acetate is an inhibitor of P-gp. No studies have been conducted with other transporter proteins.

Following oral administration of $^{14}$C-abiraterone acetate as capsules, Abiraterone acetate is hydrolyzed to Abiraterone (active metabolite). The conversion is likely through esterase activity (the esterases have not been identified) and is not CYP mediated. The two main circulating metabolites of Abiraterone in human plasma are Abiraterone sulphate (inactive) and N-oxide Abiraterone sulphate (inactive), which account for about 43% of exposure each. CYP3A4 and SULT2A1 are the enzymes involved in the formation of N-oxide Abiraterone sulphate and SULT2A1 is involved in the formation of Abiraterone sulphate.

In patients with metastatic CRPC, the mean terminal half-life of Abiraterone in plasma (mean±SD) is 12±5 hours. Following oral administration of $^{14}$C-abiraterone acetate, approximately 88% of the radioactive dose is recovered in feces and approximately 5% in urine. The major compounds present in feces are unchanged Abiraterone acetate and Abiraterone (approximately 55% and 22% of the administered dose, respectively).

The usual dose is 4 tablets (1,000 mg) taken together once a day. The tablets have to be swallowed with a glass of water on an empty stomach. The tablets have to be taken at least one hour before food, or at least 2 hours afterwards. Abiraterone has to be taken with a steroid called prednisolone to help reduce some of the side effects.

In clinical studies following the oral administration of Abiraterone acetate Abiraterone exhibited variable pharmacokinetics and an exceptionally large positive food effect. Abiraterone $C_{max}$ and $AUC_{0-\infty}$ (exposure) were increased up to 17- and 10-fold higher, respectively, when a single dose of Abiraterone acetate was administered. In order to control Abiraterone plasma concentrations Zytiga® must be taken on an empty stomach. No food should be consumed for at least two hours before the dose of Zytiga® is taken and for at least one hour after the dose of Zytiga® is taken. The administered dose is also very large with 1 g taken once daily Improving the oral bioavailability of the compound in the fasted state would therefore deliver two advantages: the abandoning of the requirement of taking the drug on an empty stomach and significant dose reduction. Based on the extent of the food effect of the currently used formula total elimination of it would allow 10-fold reduction of the dose.

In order to overcome the problems associated with prior conventional Abiraterone acetate formulations and available drug delivery systems novel complex formula of Abiraterone acetate and complexing agents and pharmaceutically acceptable excipients characterized by increased apparent solubility, instantaneous dissolution, reduced food effect which allows significant dose reduction and the abandoning of the requirement of taking the drug on an empty stomach.

A variety of strategies have been used to attempt to overcome these issues, see for example CN101768199A, CN102558275A, WO2014083512A1, WO2014145813A1, CN102321142A, WO2014102833A2, WO2014009436A1, WO2014145813A1, WO2014009434A1, WO2009009132A1, WO2013164473A1, WO1995011914A1, CA2513746A1, WO2010078300A1, WO2014100418A2 and WO2014009437A1.

DESCRIPTION OF THE INVENTION

The present disclosure relates to a stable complex comprising as active compound Abiraterone acetate or a combination of active compounds including Abiraterone acetate; and at least one complexing agent.

We have found that only the selected combinations of complexing agents and, optionally, pharmaceutically acceptable excipients disclosed in the present disclosure result in a stable complex formulae having improved physicochemical characteristics and enhanced biological performance.

The complexing agents themselves or together with the pharmaceutically accepted excipients have the function to form a complex structure with an active pharmaceutical ingredient through non-covalent secondary interactions. The secondary interactions can form through electrostatic interactions such as ionic interactions, H-bonding, dipole-dipole interactions, dipole-induced dipole interactions, London dispersion forces, π-π interactions, and hydrophobic interactions. The complexing agents, pharmaceutically accepted excipients and active ingredients are selected from the group of complexing agents, pharmaceutically accepted excipients and active ingredients which are able to form such complex structures through non-covalent secondary interactions.

In an embodiment, said complexing agent is chosen from polyethylene glycol glycerides composed of mono-, di- and triglycerides and mono- and diesters of polyethylene glycol, hydroxypropylcellulose, poloxamers, vinylpyrrolidone/vinyl acetate copolymer, polyethylene glycol, poly(2-ethyl-2-oxazoline), polyvinylpyrrolidone, block copolymers based on ethylene oxide and propylene oxide, poly(maleic acid/methyl vinyl ether), polyvinyl caprolactam-polyvinyl acetate-polyethylene glycol graft copolymer, polyoxyl 15 hydroxystearate, ethylene oxide/propylene oxide block copolymer, polyvinyl alcohol-polyethylene glycol graft copolymer, d-alpha tocopheryl polyethylene glycol 1000 succinate and caprylic/capric triglycerides.

In an embodiment, said complexing agent is chosen from polyvinylcaprolactam-polyvinyl acetate-polyethylene-glycol graft copolymers; poloxamers; polyvinylpyrrolidone; copolymers of vinylpyrrolidone and vinyl-acetate; and poly(maleic acid-co-methyl-vinyl-ether).

In an embodiment, said complexing agent is a polyvinyl caprolactam-polyvinyl acetate-polyethylene glycol graft copolymer.

In an embodiment, said polyvinyl caprolactam-polyvinyl acetate-polyethylene glycol graft copolymer is Soluplus having an average molecular weight in the range of 90,000-140,000 g/mol, having the following structure

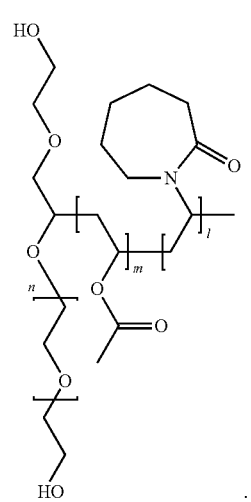

In an embodiment, said complex further comprises a pharmaceutically acceptable excipient.

In an embodiment, said pharmaceutically acceptable excipient is chosen from pharmaceutically acceptable non-ionic, anionic, cationic, ionic polymers, and surfactants.

In an embodiment, said excipient is selected from the group of sodium laury sulfate, poloxamer, sodium acetate, citric acid and sodium deoxycholate (SDC).

In an embodiment, said excipient is sodium deoxycholate (SDC).

In some embodiments, the compositions may additionally include one or more pharmaceutically acceptable excipients, auxiliary materials, carriers, active agents or combinations thereof.

In an embodiment, said complex has a particle size less than 600 nm.

In an embodiment said complex has a particle size in the range between 50 nm and 600 nm.

In an embodiment said complex has a particle size in the range between 100 nm and 500 nm.

In an embodiment, said complex is instantaneously redispersible in physiological relevant media.

In an embodiment, said complex has increased dissolution rate compared to the commercially available form of Abiraterone acetate (Zytiga).

In an embodiment, said complex is stable in solid form and in colloid solution and/or dispersion.

In an embodiment, said complex's apparent solubility in water is at least 0.6 mg/mL.

In an embodiment, said complex exhibits X-ray amorphous character in the solid form.

In an embodiment, said complex has a permeability of $0.5 \times 10^{-6}$ cm/s in a parallel artificial membrane permeability assay (PAMPA).

In an embodiment, said complex exhibits no positive food effect which allows significant dose reduction and the abandoning of the requirement of taking the drug on an empty stomach.

In an embodiment, said complex exhibits no positive food effect based on in-vivo dog and clinical studies.

In an embodiment, the variability of exposure of the complex is significantly reduced compared to the commercially available form (Zytiga).

In an embodiment said complex comprises
a) Abiraterone acetate; or a combination of active compounds including Abiraterone acetate;
b) polyvinyl caprolactam-polyvinyl acetate-polyethylene glycol graft copolymer as a complexing agent; and
c) sodium deoxycholate as an excipient.

In an embodiment said complex comprises 5 to 40% by weight of Abiraterone acetate.

In an embodiment said complex comprises 5 to 80% by weight of a polyvinylcaprolactam-polyvinyl acetate-polyethylene-glycol graft copolymer.

In an embodiment said complex comprises 0.1 to 50% by weight of sodium deoxycholate.

In an embodiment said complex comprises
a) 5 to 40% by weight of Abiraterone acetate;
b) 5 to 80% by weight of a polyvinylcaprolactam-polyvinyl acetate-polyethylene-glycol graft copolymer; and
c) 0.1 to 50% by weight of sodium deoxycholate.

In an embodiment, said complex further comprises an additional active agent chosen from agents useful in the treatment of early stage and metastatic prostate cancer and advanced breast cancer.

In an embodiment, said complex further comprises one or more additional active agents selected from Rifampicin, Prednisone/Prednisolone, Dexamethasone, Ketoconazole, Testosterone Enanthate, Enzalutamide, Dextromethorphan hydrobromide, Dexamethasone, Exemestane, Goserelin, Degarelix, Veliparib, Dovitinib, Leuprolide, Alisertib, cabozantinib, Cabazitaxel, Dasatinib, Glucocorticoid, Docetaxel, Dutasteride, Hydroxychloroquine, Ipilimumab, Metformin, Sunitinib, Selinexor, Everolimus, Trastuzumab, Tamoxifen, and combinations thereof.

In an embodiment, said complex is characterized by infrared (ATR) spectrum having main/characteristic absorption peaks at least at 569 $cm^{-1}$, 607 $cm^{-1}$, 713 $cm^{-1}$, 797 $cm^{-1}$, 843 $cm^{-1}$, 942 $cm^{-1}$, 973 $cm^{-1}$, 1030 $cm^{-1}$, 1103 $cm^{-1}$, 1148 $cm^{-1}$, 1195 $cm^{-1}$, 1241 $cm^{-1}$, 1333 $cm^{-1}$, 1371 $cm^{-1}$, 1421 $cm^{-1}$, 1441 $cm^{-1}$, 1477 $cm^{-1}$, 1336 $cm^{-1}$, 1734 $cm^{-1}$, 2858 $cm^{-1}$, 2928 $cm^{-1}$ characteristic absorption peaks.

In an embodiment, said complex is characterized by Raman spectrum having main/characteristic absorption peaks at least at 239 $cm^{-1}$, 581 $cm^{-1}$, 701 $cm^{-1}$, 797 $cm^{-1}$, 846 $cm^{-1}$, 1026 $cm^{-1}$, 1088 $cm^{-1}$, 1196 $cm^{-1}$, 1264 $cm^{-1}$, 1445 $cm^{-1}$, 1584 $cm^{-1}$, 1600 $cm^{-1}$, 1735 $cm^{-1}$ characteristic absorption peaks.

Disclosed herein is a process for the preparation of a stable complex of Abiraterone acetate, said process comprising the step of mixing a solution of the active agent and at least one complexing agent and optionally one or more pharmaceutically acceptable excipient in a pharmaceutically acceptable solvent with an aqueous solution containing optionally least one pharmaceutically acceptable excipient.

In an embodiment said complex is obtained via a mixing process.

In an embodiment said complex is obtained via a continuous flow mixing process.

In an embodiment said process is performed in a continuous flow instrument.

In an embodiment said continuous flow instrument is a microfluidic flow instrument.

In an embodiment, said complex is not obtained via a milling process, by high pressure homogenization process, encapsulation process or solid dispersion process.

In an embodiment said pharmaceutically acceptable solvent is chosen from water, methanol, ethanol, isopropanol, n-propanol, acetone, acetonitrile, dimethyl-sulfoxide, tetrahydrofuran, or combinations thereof.

In an embodiment, said pharmaceutically acceptable solvent is a combination of water and tetrahydrofuran.

In an embodiment said solvents are miscible with each other and the aqueous solvent comprises 0.1 to 99.9% weight of the final solution.

In an embodiment, said aqueous solvent comprises 0.1 to 99.9% weight of the final solution.

In an embodiment, said aqueous solvent comprises 50 to 90% weight of the final solution.

In an embodiment, said aqueous solvent comprises 50 to 80% weight of the final solution.

In an embodiment, said aqueous solvent comprises 50 to 70% weight of the final solution.

In an embodiment, said aqueous solvent comprises 50 to 60% weight of the final solution.

In an embodiment, said aqueous solvent comprises 50% weight of the final solution.

In an embodiment, said aqueous solvent comprises 10 to 40% weight of the final solution.

In an embodiment, said aqueous solvent comprises 10 to 30% weight of the final solution.

In an embodiment, said aqueous solvent comprises 10 to 20% weight of the final solution.

In an embodiment, said aqueous solvent comprises 10% weight of the final solution.

In an embodiment said complex further comprises a pharmaceutically acceptable carrier.

In an embodiment said composition is suitable for oral, pulmonary, rectal, colonic, parenteral, intracisternal, intravaginal, intraperitoneal, ocular, otic, local, buccal, nasal, or topical administration.

In an embodiment said composition is suitable for oral administration.

Disclosed herein is a complex for use in the manufacture of a medicament for the treatment of prostate cancer and advanced breast cancer.

Disclosed herein is a complex for use for the treatment of prostate cancer and advanced breast cancer.

In an embodiment, a method for reducing the therapeutically effective dosage of Abiraterone acetate compared to Zytiga® tablets comprises oral administration of a pharmaceutical composition as described herein.

The present disclosure relates to a stable complex comprising as active compound Abiraterone acetate or a combination of active compounds including Abiraterone acetate; and at least one complexing agent chosen from polyvinylcaprolactam-polyvinyl acetate-polyethylene-glycol graft copolymers; poloxamers; polyvinylpyrrolidone; copolymers of vinylpyrrolidone and vinyl-acetate; and poly(maleic acid-co-methyl-vinyl-ether); said complex characterized in that it has a particle size less than 600 nm and possesses at least one of the following properties:
  a) is instantaneously redispersible in physiological relevant media;
  b) has increased dissolution rate compared to the commercially available form of Abiraterone acetate (Zytiga);
  c) is stable in solid form and in colloid solution and/or dispersion;
  d) apparent solubility in water of at least 0.6 mg/mL;
  e) has a PAMPA permeability of at least $0.5 \times 10^{-6}$ cm/s when dispersed in distilled water, which does not decrease in time at least for 3 months;
  f) exhibits no positive food effect which allows significant dose reduction and the abandoning of the requirement of taking the drug on an empty stomach; and
  g) the variability of exposure of the complex is significantly reduced compared to the commercially available form (Zytiga).

In an embodiment, said complex possesses at least two of the properties described in a)-g).

In an embodiment, said complex possesses at least three of the properties described in a)-g).

In an embodiment, said complex has an apparent solubility in water of at least 0.6 mg/mL and exhibits no positive food effect which allows significant dose reduction and the abandoning of the requirement of taking the drug on an empty stomach.

In an embodiment, said complex has a PAMPA permeability of at least $0.5 \times 10^{-6}$ cm/s and exhibits no positive food effect which allows significant dose reduction and the abandoning of the requirement of taking the drug on an empty stomach.

In an embodiment, said complex has an apparent solubility in water of at least 0.6 mg/mL and a PAMPA permeability of at least $0.5 \times 10^{-6}$ cm/s.

In an embodiment, said complex has an apparent solubility in water of at least 0.6 mg/mL, PAMPA permeability of at least $0.5 \times 10^{-6}$ cm/s and exhibits no positive food effect which allows significant dose reduction and the abandoning of the requirement of taking the drug on an empty stomach.

In an embodiment, said complexing agent which is a polyvinylcaprolactam-polyvinyl acetate-polyethylene-glycol graft copolymer and pharmaceutically acceptable excipient which is sodium deoxycholate comprise 10 weight % to about 95 weight % of the total weight of the complex.

In another aspect the complexing agents and/or pharmaceutically acceptable excipients are associated or interact with the Abiraterone acetate as the result of the mixing process. In an embodiment, said mixing process is a continuous flow mixing process.

In some embodiments, the structure of the complex Abiraterone acetate formula is different from the core-shell type milled particle, precipitated encapsulated particles, micelles and solid dispersions.

The pharmaceutical composition of the disclosure can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

In an embodiment, said compositions can be formulated by adding different types of pharmaceutically acceptable excipients for oral administration in solid, liquid, local (powders, ointments or drops), or topical administration, and the like.

In an embodiment, said dosage form is a solid dosage form.

Solid dosage forms for oral administration include, but are not limited to, capsules, tablets, pills, powders, and granules. In such solid dosage forms, the active agent is admixed with at least one of the following excipients: (a) one or more inert excipients (or carriers), such as sodium citrate or dicalcium phosphate; (b) fillers or extenders, such as starches, lactose, sucrose, glucose, mannitol, microcrystalline cellulose and silicic acid; (c) binders, such as cellulose derivatives, alginates, gelatin, polyvinylpyrrolidone, sucrose and acacia; (d) humectants, such as glycerol; (e) disintegrating agents, such as crospovidon, sodium starch glycolate, effervescent compositions, croscarmellose sodium, calcium carbonate, potato or tapioca starch, alginic acid, certain complex silicates and sodium carbonate; (f) solution retarders, such as acrylates, cellulose derivatives, paraffin; (g) absorption accelerators, such as quaternary ammonium compounds; (h) wetting agents, such as polysorbates, cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Besides such inert diluents, the composition can also include adjuvants, such as wetting agents, emulsifying and suspending agents, sweetening, flavoring, and perfuming agents.

Advantages of the complex Abiraterone acetate formulae of the disclosure include, but are not limited to (1) physical and chemical stability, (2) instantaneous redispersibility, (3) stability in colloid solution or dispersion in the therapeutic time window, (4) increased apparent solubility compared to the conventional Abiraterone acetate formulation (Zytiga), (5) increased permeability, (6) increased oral bioavailability in fasted state, and (7) no positive food effect.

In an embodiment, solid form of said complex has good processability for the preparation of any type of pharmaceutical dosage form.

In an embodiment, said complex has good/instantaneous redispersibility of solid complex formulae of Abiraterone acetate in water, biologically relevant media, e.g. SGF, FessiF and FassiF media and gastro intestinal fluids and adequate stability in colloid solutions and/or dispersion in the therapeutic time window.

In an embodiment, said complex has increased apparent solubility and permeability compared to the commercially available dosage form (Zytiga). In some embodiments, the apparent solubility and permeability of the complex Abiraterone acetate formulae is at least 0.6 mg/mL and $0.5 \times 10^{-6}$ cm/s, respectively.

BRIEF DESCRIPTION OF THE DRAWINGS

FIG. 1 shows the complexing agent screening for formula selection in order to select the formulae having instantaneous redispersibility.

EXAMPLES

Several pharmaceutically acceptable complexing agents and pharmaceutically acceptable excipients and their combinations were tested in order to select the formulae having instantaneous redispersibility as shown in FIG. 1. One of the examples that displayed an acceptable level of redispersibility was selected for further analysis.

Figure 2:
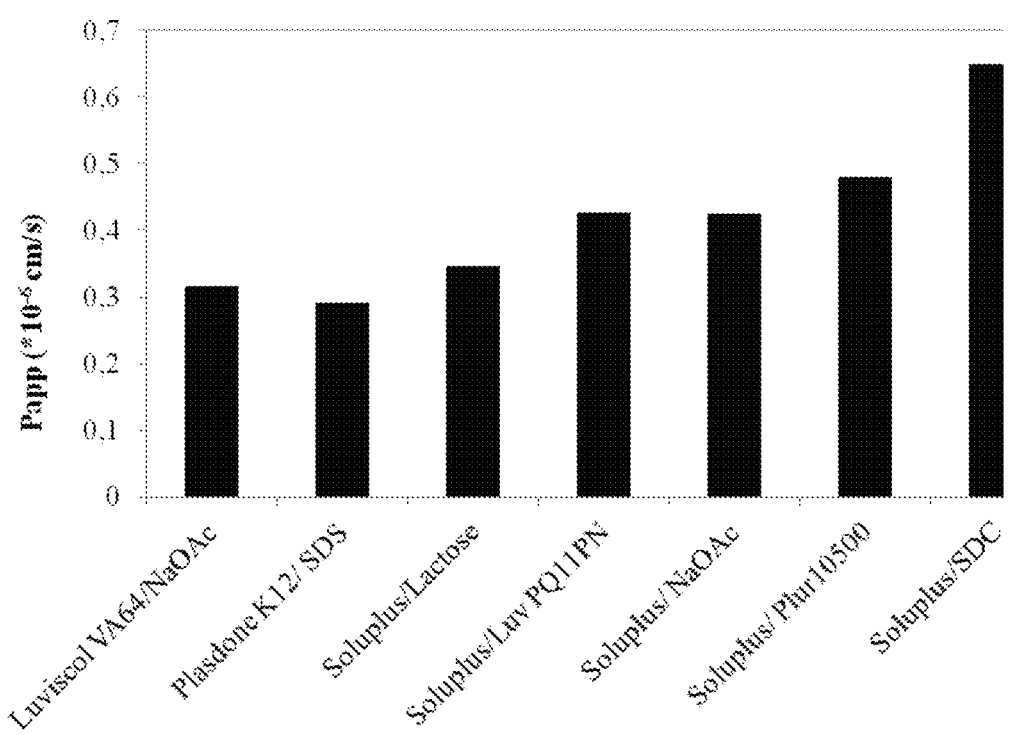
FIG. 2 shows comparative PAMPA assays of complex Abiraterone acetate formulations consisting of different pharmaceutically acceptable excipients.

PAMPA permeability of the selected formulations was measured in order to select the complex Abiraterone acetate formulation having the best in-vitro performance (FIG. 2). PAMPA permeability measurements were performed as described by M Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 1-24 hours. The concentration in the receiver compartment was determined by UV-VIS spectrophotometry (Thermo Scientific Genesys S10).

Figure 3:
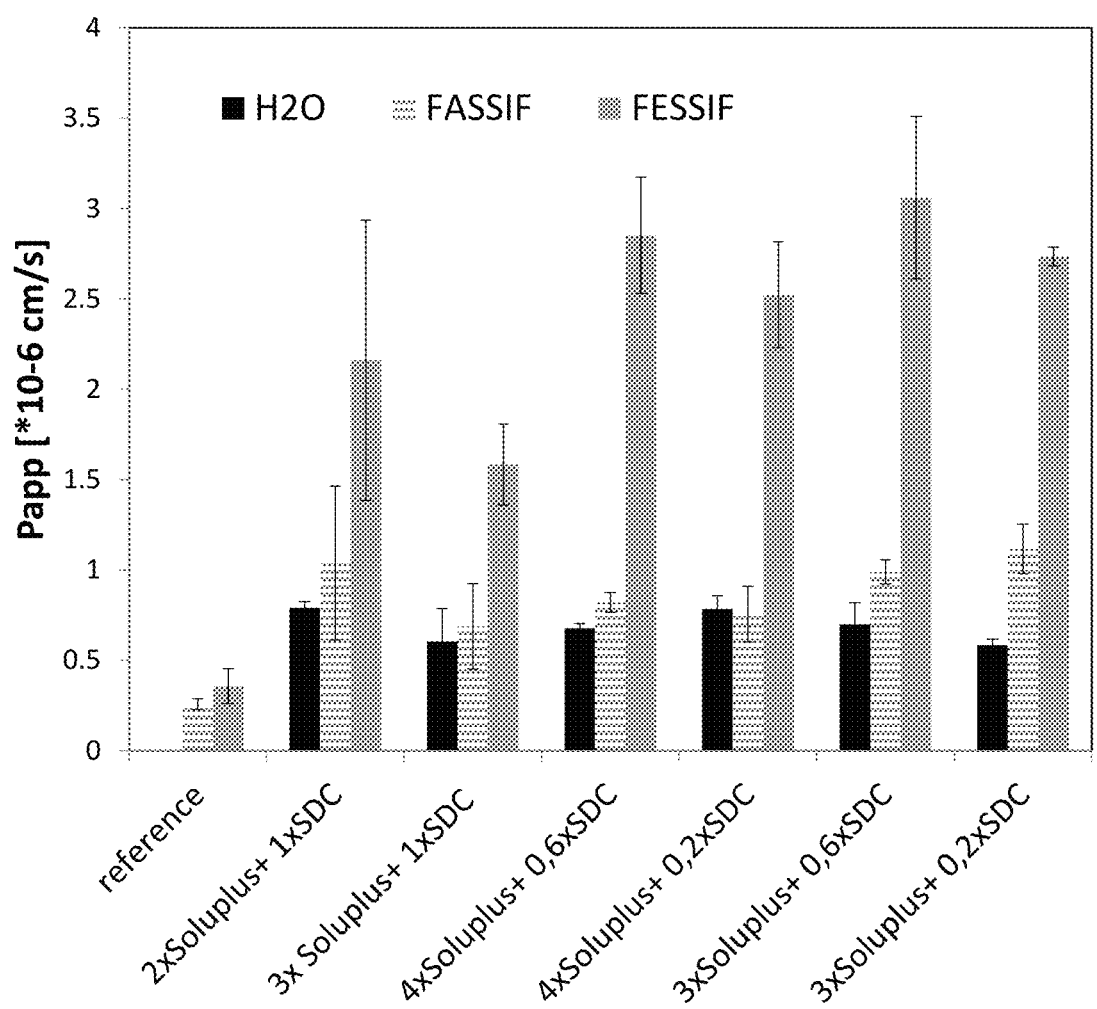
FIG. 3 shows comparative PAMPA assays of complex Abiraterone acetate formulations containing complexing agent and pharmaceutically acceptable excipient in different ratios.

Polyvinylcaprolactam-polyvinyl acetate-polyethylene-glycol graft copolymer (Soluplus) as complexing agent and sodium deoxycholate (SDC) as pharmaceutically accepted excipient were selected to form complex Abiraterone acetate formulation having improved material characteristics. Based on the in-vitro properties (redispersibility profile, stability of the redispersed solution and PAMPA permeability) (Table 1 and FIG. 3) the optimal ratio of Abiraterone acetate, polyvinylcaprolactam-polyvinyl acetate-polyethylene-glycol graft copolymer (Soluplus) and sodium deoxycholate (SDC) in the complex formulation of the present disclosure was found to be 1:4:0.6.

TABLE 1 shows comparative PAMPA assays of complex Abiraterone acetate
formulations containing different amount of Soluplus and SDC
in different ratios

| SDC ratio to Abiraterone acetate | Soluplus ratio to Abiraterone acetate | | |
|---|---|---|---|
| | 2X | 3X | 4X |
| | Redispersibility and stability | | |
| 0.2X | not dispersable | dispersable, unstable | dispersable, unstable |
| 0.6X | not dispersable | dispersable, stable | dispersable, stable |
| 1X | dispersable, unstable | dispersable, stable | dispersable, stable |
| | PAMPA permeability ($10^{-6}$ cm/s) | | |
| 0.2X | 0.504 | 0.584 | 0.784 |
| 0.6X | 0.665 | 0.699 | 0.677 |
| 1X | 0.629 | 0.604 | — |

The technological approach applied to the manufacture powder of the complex Abiraterone acetate formulation of the present invention relied on freeze-drying or spray-drying of the colloid solution of complex Abiraterone acetate formulation containing selected complexation agent(s), pharmaceutically acceptable excipient(s) and the active drug substance. The colloid solution of complex Abiraterone acetate formulation of the present invention was prepared by continuous flow mixing of two solutions. One of the solutions contained the Abiraterone acetate and the complexation agent(s). The second solution was water and contains the pharmaceutically acceptable excipient(s). The colloid solution was solidified right after the preparation. Properties of the produced colloid solution could be modified during the process by precise control and optimization of various transformation parameters (e.g. temperature, flow rate and concentration).

Colloid solutions of Abiraterone acetate complex formulation of the present disclosure were prepared by continuous mixing process using Solution 1/a,b,c containing Abiraterone acatetae and Soluplus® and Solution 2/a,b,c containing sodium deoxycholate (SDC) as shown in 2. The optimized Abiraterone acetate: excipients ratio of the complex Abiraterone acetate formulation (1:4:0.6) was kept constant. Different flow rate ratios were tested in order to determine the optimal manufacturing condition. The total flow rate of the production (sum of the Solvent 1 and Solvent 2 flow rates) and the amount of the colloid solution collected were kept constant at 50.0 mL/min and 25.0 mL, respectively. The appearance of the produced colloid solution and the stability of the redispersed complex Abiraterone acetate formulations were used to determine the optimal parameters of the production. Table 3 summarizes the results.

TABLE 2 shows the composition of the solution used for the production
of the colloid solutions of Abiraterone acetate complex formulation
of the present disclosure.

| | Solvent | Concentration of Components | |
|---|---|---|---|
| Solution 1/a | Tetrahydrofuran | Abiraterone acetate 10 mg/mL | Soluplus ® 40 mg/mL |
| Solution 1/b | Tetrahydrofuran | Abiraterone acetate 20 mg/mL | Soluplus ® 80 mg/mL |
| Solution 1/c | Tetrahydrofuran | Abiraterone acetate 40 mg/mL | Soluplus ® 160 mg/mL |
| Solution 2/a | purified water | Sodium deoxycholate 1.500 mg/mL | — |
| Solution 2/b | purified water | Sodium deoxycholate 1.340 mg/mL | — |
| Solution 2/c | purified water | Sodium deoxycholate 1.260 mg/mL | — |

TABLE 3 shows effect of the flow rate ratio on the appearance and stability
of the redispersed formulae.

| Solution 1 | Solution 2 | Solvent 1:Solvent 2 ratio | Appearance of redispersed formulation |
|---|---|---|---|
| Solution 1/a | Solution 2/a | 1:4 | milky solution |
| Solution 1/b | Solution 2/b | 1:9 | milky solution |
| Solution 1/c | Solution 2/c | 1:19 | milky solution |

Figure 4:
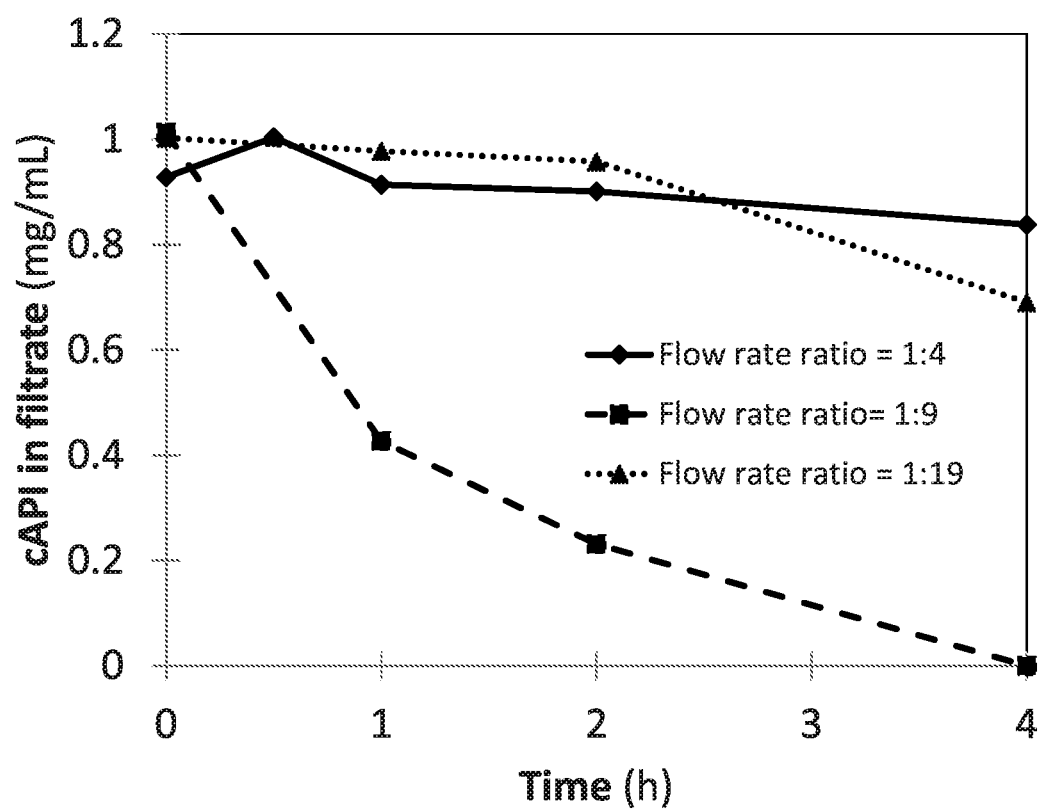
FIG. 4. shows the stability of the redispersed complex Abiraterone acetate formulation prepared with different flow rate ratios.

The stability of the redispersed freeze-dried samples was monitored. Solid formulations of complex Abiraterone acetate were redispersed in purified water or in biorelevant media using 1 mg/mL concentration for the Abiraterone acetate. The stability of redispersed formulations was monitored by filtering it with 0.45 µm pore size filter at different time points. The Abiraterone acetate contents of the filtrates were determined by UV-VIS spectrophotometry (VWR UV-3100 PC) (FIG. 4). Flow rate ratio of 1:4 was found to be optimal for the production of complex Abiraterone acetate formulation of the present disclosure.

Figure 5:
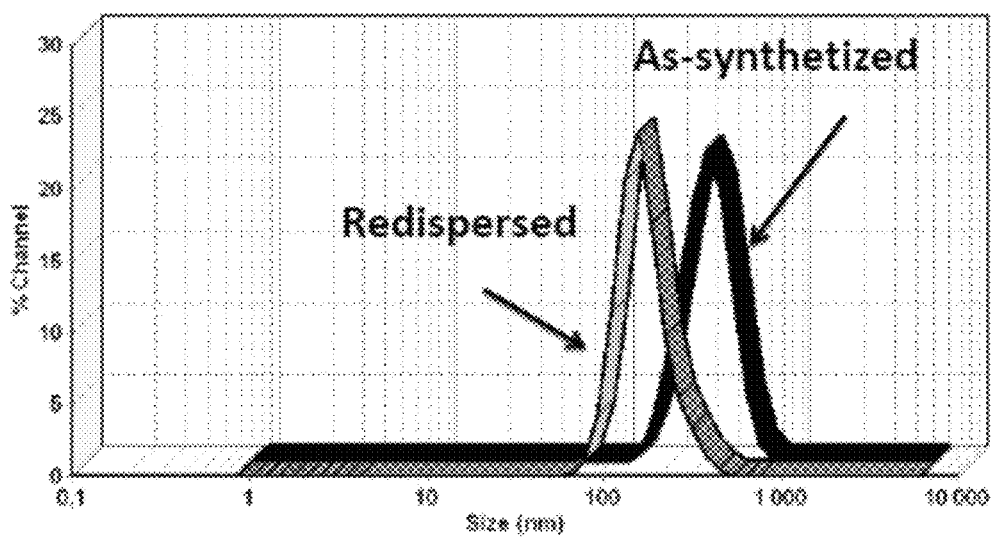
FIG. 5 shows the particle size distribution of the as-synthesized colloid solution and redispersed solid complex of the selected formula.

A colloid solution of Abiraterone acetate complex formula (Formulation 1) with the optimal ratio of the complexing agent and pharmaceutically acceptable excipient of the present disclosure was prepared by continuous flow mixing in a flow instrument. As a starting solution, 1000 mg Abiraterone acetate and 4000 mg polyvinylcaprolactam-polyvinyl acetate-polyethylene-glycol graft copolymer (Soluplus) dissolved in 100 mL tetrahydrofuran was used. The prepared solution was passed into the instrument with 10 mL/min flow rate. Meanwhile, aqueous solvent containing 750 mg sodium deoxycholate in 500 mL water was passed into the instrument with 40 mL/min flow rate, where Abiraterone acetate formed complex Abiraterone acetate composition. The colloid solution of the complex Abiraterone acetate is continuously produced at atmospheric pressure. The produced colloid solution was frozen on dry-ice and then it was lyophilized using a freeze drier equipped with −110° C. ice condenser, with a vacuum pump. For the process monitoring particle size and size distribution of the complex Abiraterone acetate formula was used. Particle size and size distribution of the colloid solution right after the production and the reconstituted solid complex Abiraterone acetate formula are seen in Error! Reference source not found. It was found to be D(50)=310 nm for the produced colloid solution and D(50)=158 nm for the redispersed particles, respectively (FIG. 5).

Figure 6:
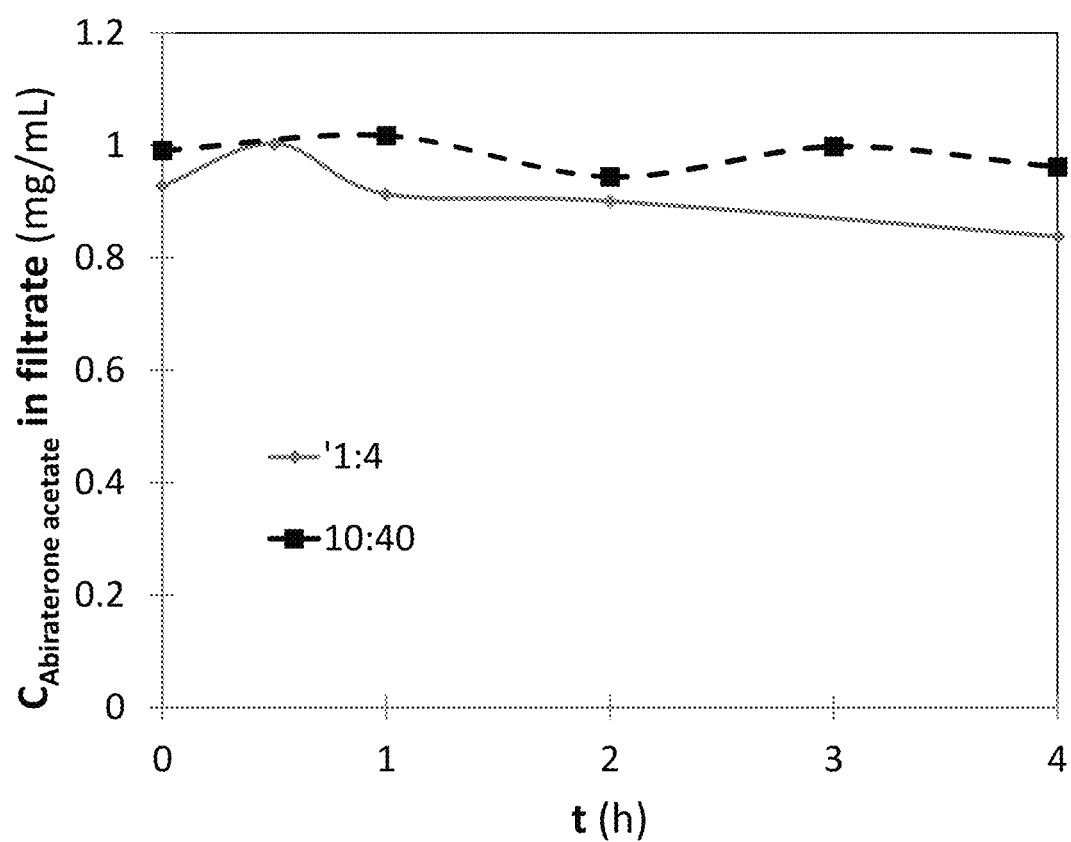
FIG. 6. shows stability of the redispersed complex Abiraterone acetate formulation prepared with intensified process flow rates.

Process intensification was performed in order to increase the efficiency of the production. The flow rate ratio was increased from 1:4 to 10:40. The produced colloid solution of the complex Abiraterone acetate formulation of the present disclosure was solid formulated using freeze-drying method as described above. The samples were reconstituted using purified water. The physical stability of redispersed solution was also monitored in time by the determination of the Abiraterone acetate content of the redispersed solution after filtration (FIG. 6). Process intensification did not have effect on the stability of the redispersed solution.

With 5:20 flow rate ratio, solvent mixture containing novel Abiraterone acetate complex formulation (Formulation 1) was prepared and solid formulated using freeze-drying method. The stability of the freeze-dried powder was tested after one week storage at 4° C. The samples were reconstituted using purified water. The results showed that the Abiraterone acetate content of the filtrate right after the production was identical to Abiraterone acetate content of the filtrate after one week storage within the experimental accuracy. The Abiraterone acetate content of the filtrates slightly decreases in time; however it does not have effect on the appearance and redispersibility of the freeze-dried powder.

Figure 7:
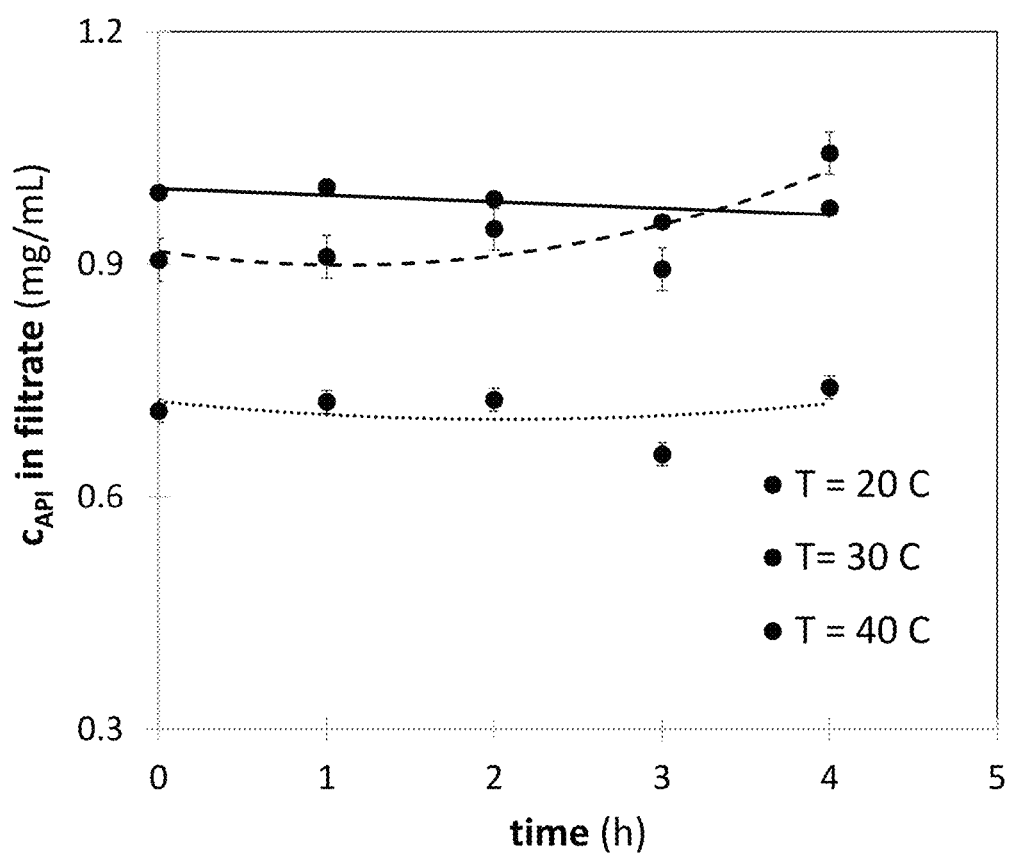
FIG. 7 shows the effect of the production temperature on the Abiraterone acetate content of the filtrate of the redispersed Complex Abiraterone acetate formulation.

The effect of the production temperature on the product quality was investigated. Colloid solution of complex Abiraterone acetate formulation of the present disclosure was prepared using the intensified and optimized parameter sets described above at 20-, 30- and 40° C. temperatures. The colloid solutions produced were then freeze-dried. The freeze-dried samples were redispersed in purified water and their stability was monitored in time as previously described (FIG. 7). Optimal production temperature was found to be 30° C.

Comparative Formulation Studies

Crystalline Abiraterone acetate was wet milled in the presence of polyvinyl caprolactam-polyvinyl acetate-polyethylene glycol graft copolymer (Soluplus) and Sodium deoxycholate in order to produce nanosized Abiraterone acetate particles. The milling process was carried out using a Fritsch Pulverisette 6 instrument. Volume of $Si_2N_3$ milling vessel was 250 mL. 25 milling balls with 10 mm diameter was used. Milling speed was set to be 500 rpm. 5×1 h milling time was applied.

Milled suspension contained 0.447 g Abiraterone acetate, 1.178 g Soluplus and 0.267 g Sodium deoxycholate in 12.5 mL MilliQ water. The wet milling process resulted in a foam-like suspension which was freeze-dried to obtain solid powder.

Dissolution profile of wet milled Abiraterone was compared with the dissolution of crystalline Abiraterone acetate and complex Abiraterone acetate of the present disclosure at 37° C. 10 mg Abiraterone acetate equivalent samples were dispersed in 20 mL FaSSIF (fasted) and FeSSIF (fed) media and were filtered by 20 nm disposable syringe filter. The active content in the filtrate was measured by UV-Vis spectrophotometry.

Figure 8:
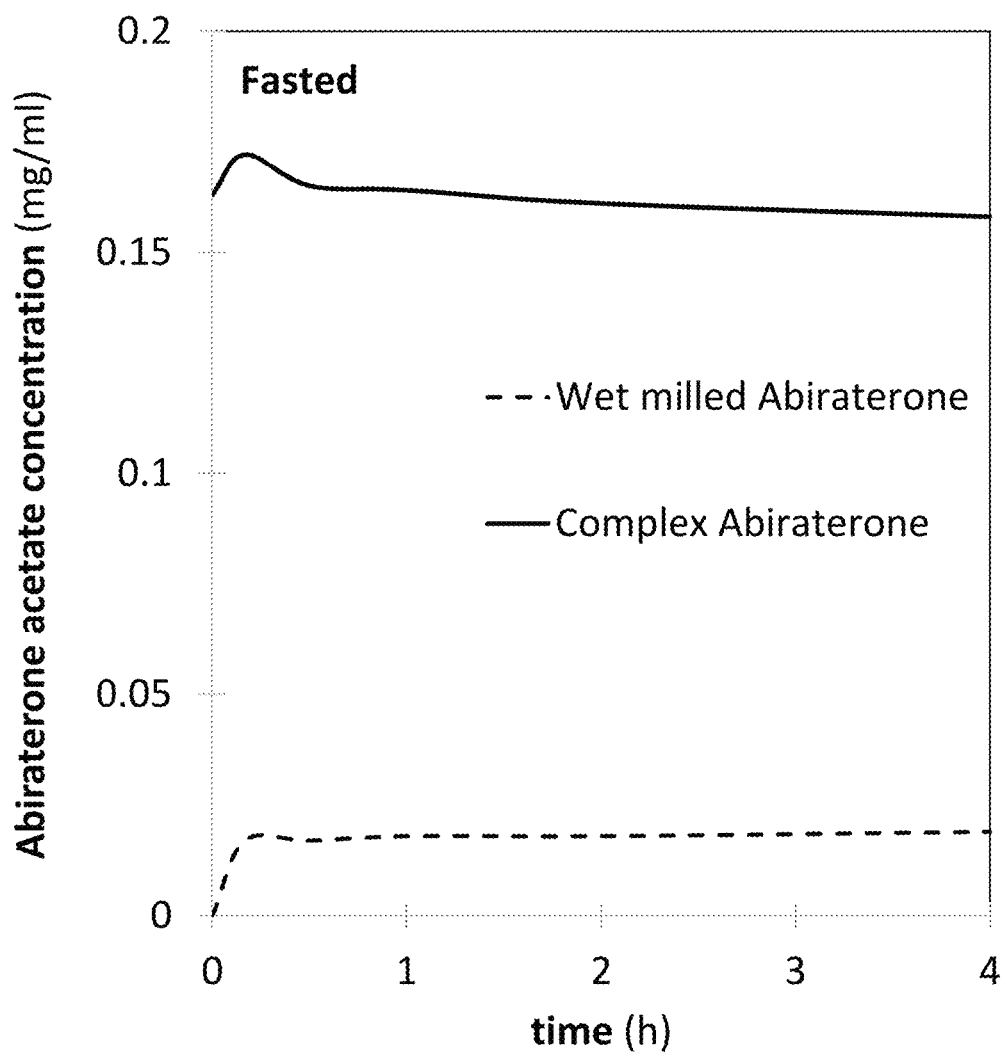
FIG. 8 shows dissolution profile of wet milled Abiraterone acetate and complex Abiraterone acetate in FaSSIF medium.
Figure 9:
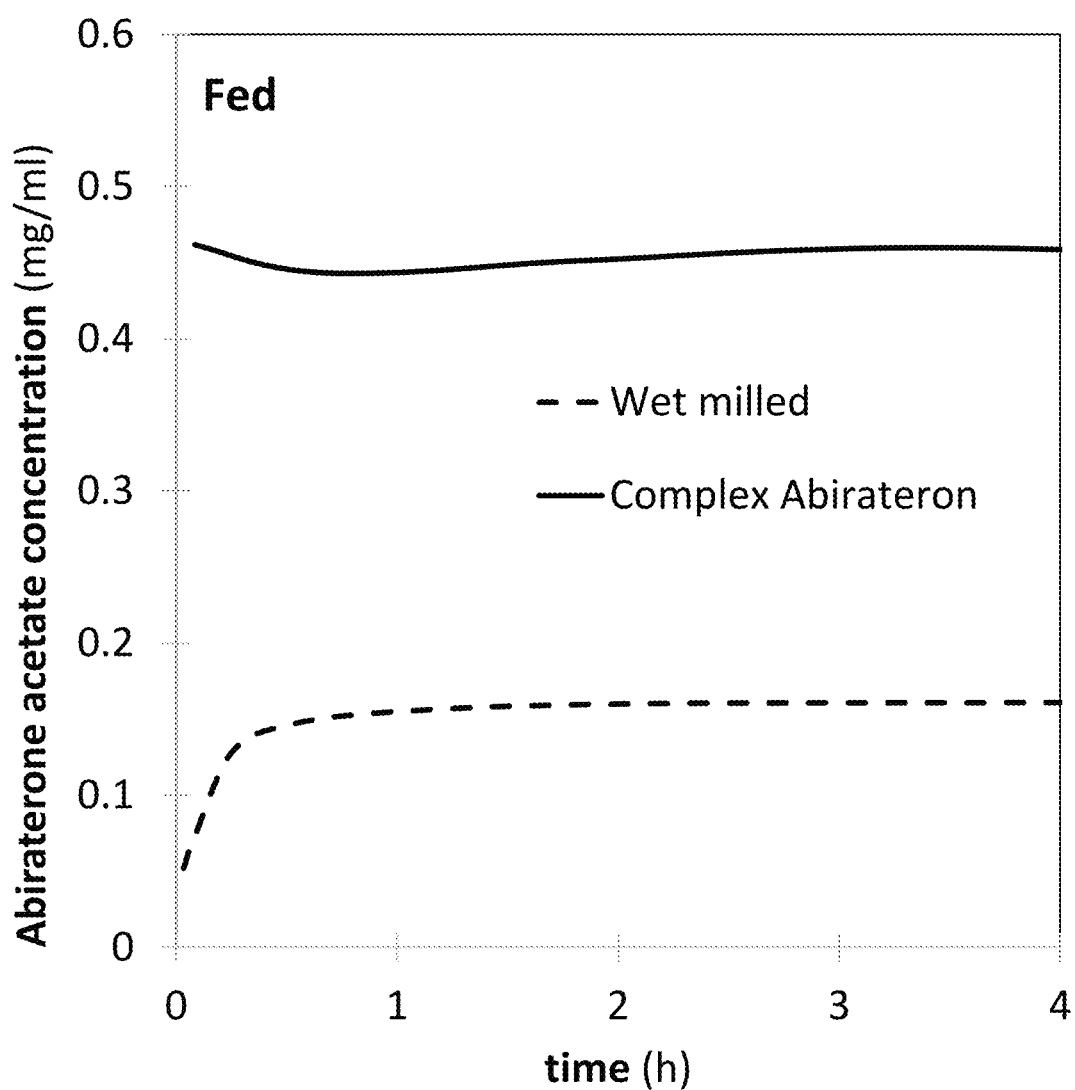
FIG. 9 shows dissolution profile of wet milled Abiraterone acetate and complex Abiraterone acetate in FeSSIF medium.
Figure 10:
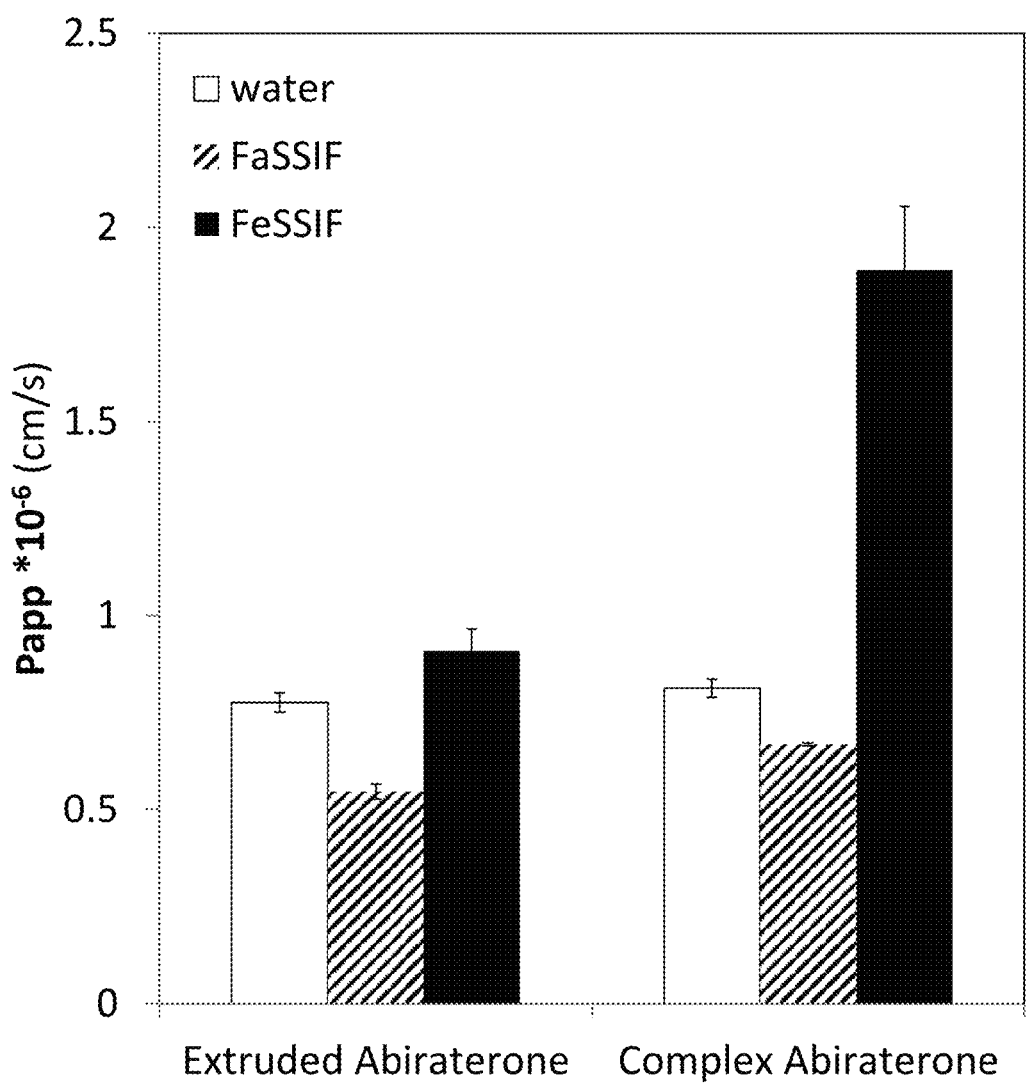
FIG. 10 shows PAMPA permeability of extruded Abiraterone acetate formulation and complex Abiraterone formulation of the present disclosure.

Abiraterone acetate dissolution from the complex Abiraterone acetate formulation of the present disclosure is 3-fold higher in FeSSIF and 9-fold higher in FaSSIF compared to the dissolved amount of Abiraterone acetate from the wet milled samples (FIG. 8 and FIG. 9). Pharmaceutical formulation of Abiraterone acetate was prepared by extrusion technique using polyvinyl caprolactam-polyvinyl acetate-polyethylene glycol graft copolymer (Soluplus) and Sodium deoxycholate as pharmaceutically acceptable excipients. The extrusion was carried out using HAAKE™ MiniLab II Micro Compounder (Thermo Scientific) instrument. In a premixing step, dry powders (17.9 w/w % Abireterone-acetate, 71.4 w/w % Soluplus, 10.7 w/w % SDC) were mixed in a mortar then 8 g powder mixture was fed into the extruder. The extrusion was performed at 130° C. with a screw rate of 20 rpm. PAMPA permeability of the extruded Abiraterone acetate formulation was compared to the PAMPA permeability of complex Abiraterone acetate formulation of the present disclosure in water, FaSSIF and FeSSIF media. PAMPA permeability of complex Abiraterone acetate was 2-fold higher in FeSSIF medium than the permeability of the extruded formulation (FIG. 10).

Comparative Solubility Tests

The apparent solubility of complex Abiraterone acetate formula and unformulated compounds was measured by UV-VIS spectroscopy at room temperature. The samples were dispersed in distillated water and the resulting dispersions were filtered by 100 nm disposable syringe filter. The active content in the filtrate was measured by UV-Vis spectrophotometry and the solubility was calculated. The filtrate may contain Abiraterone acetate complex particles which could not be filtrated out using 100 nm pore size filter.

Solubility of complex Abiraterone acetate formula and unformulated compound was 0.6 mg/mL and <0.004 mg/mL, respectively.

Comparative In-Vitro PAMPA Assays

PAMPA permeability of complex Abiraterone acetate formula was above $0.5 \times 10^{-6}$ cm/s, while it was below $0.1 \times 10^{-6}$ cm/s for the unformulated compound.

Stability of the Colloid Solution in the GI Tract

Figure 11:
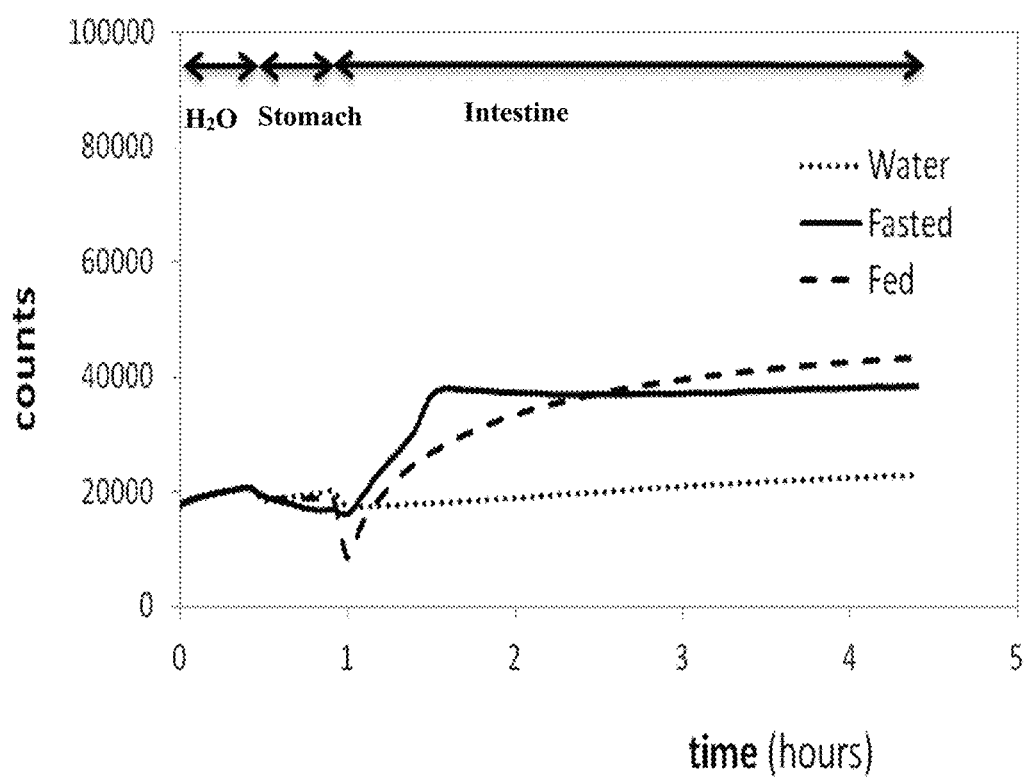
FIG. 11 shows the stability of the colloid solution in simulated fasted and fed state.

A simulated passage through the GI tract was performed in order to detect any instability of the colloid solution at pH values and bile acid concentrations representative of the GI tract in the fasted and in the fed conditions. No significant change in light scattering of the colloid solution was observed in the simulation indicating that the complex Abiraterone formula will be stable under these conditions in the time window of the absorption process in both the fasted and in the fed conditions (FIG. 11).

Comparative Dissolution Tests

Figure 12:
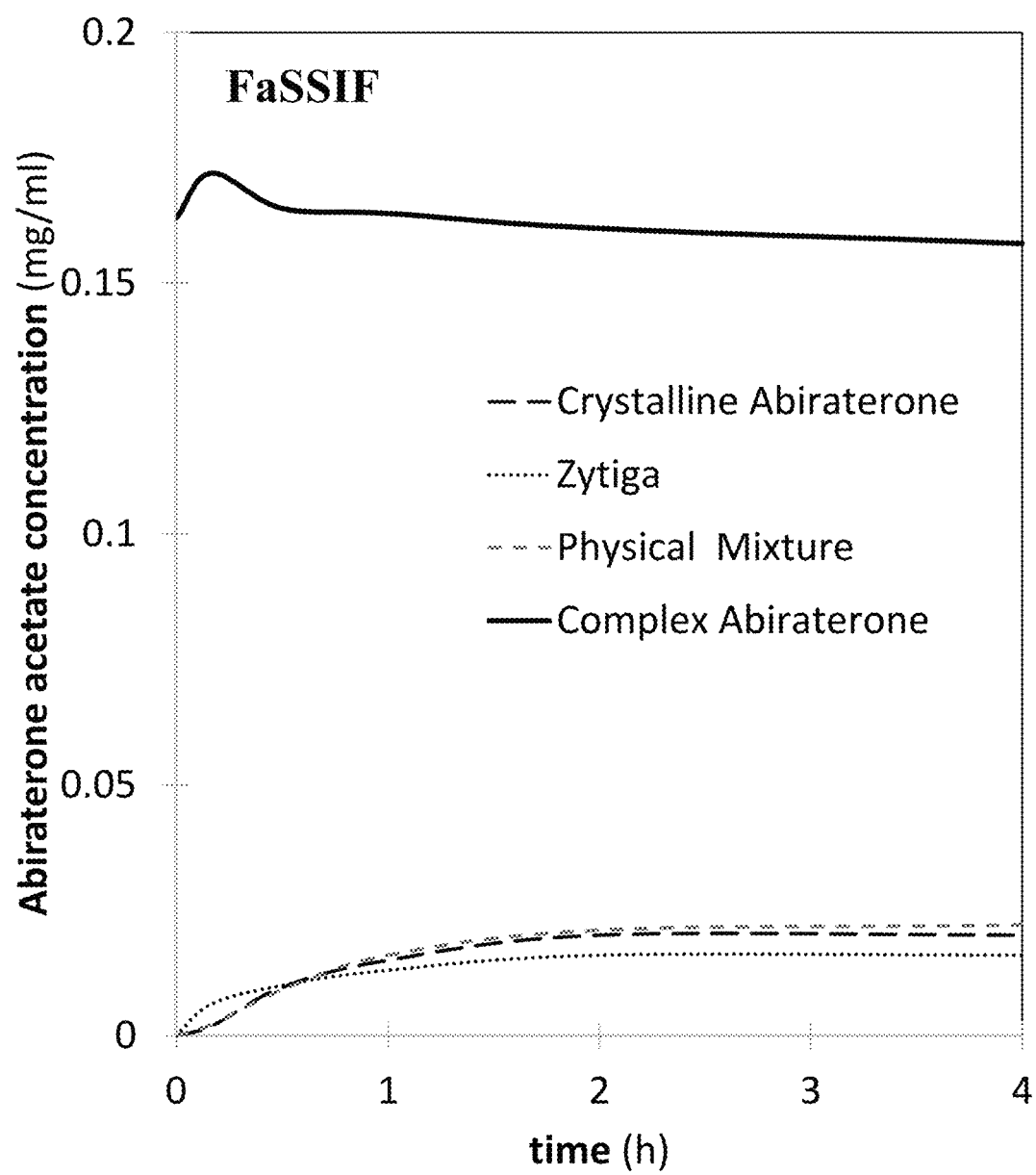
FIG. 12 shows dissolution profile of crystalline Abiraterone acetate, physical mixture, Zytiga and complex Abiraterone acetate in FaSSIF medium.
Figure 13:
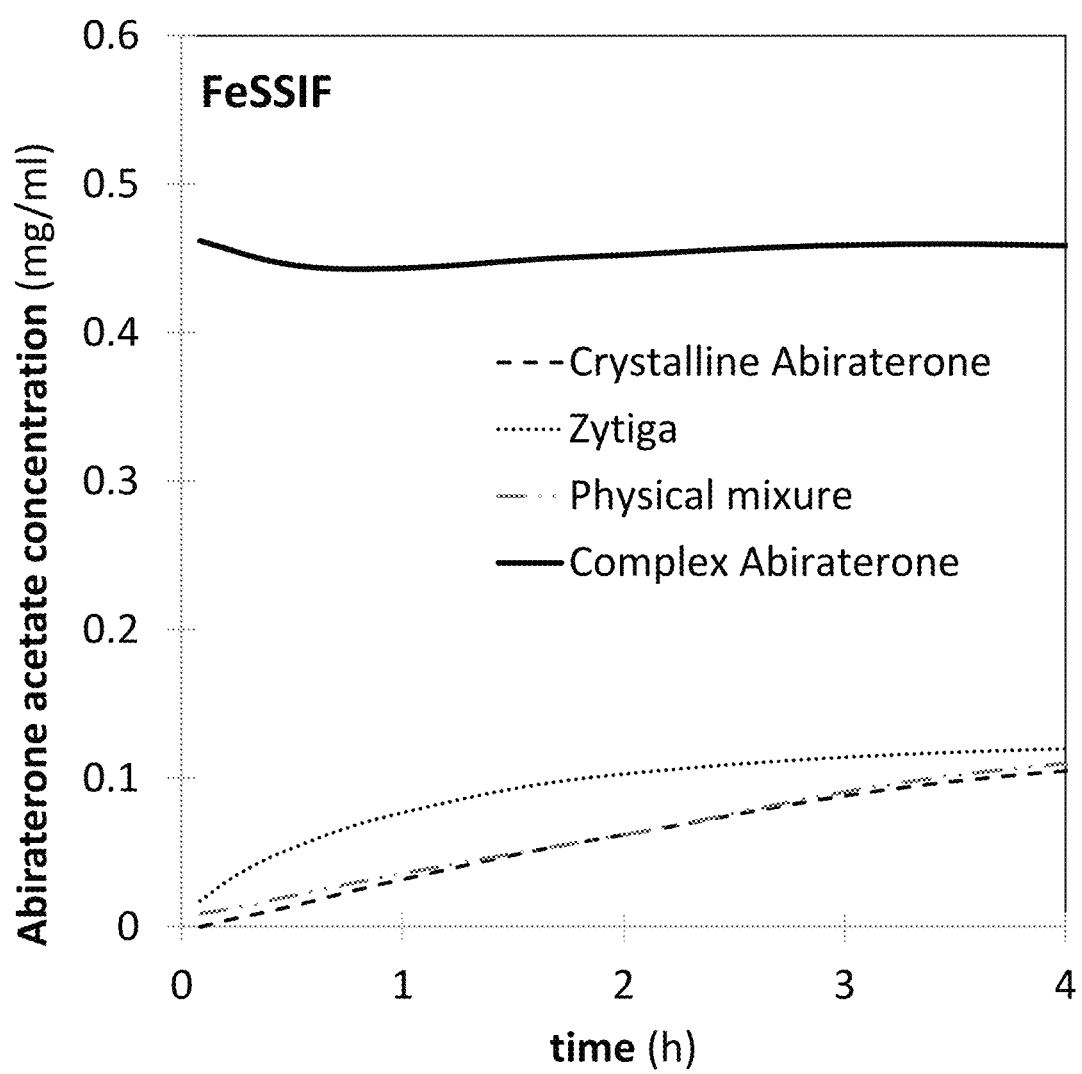
FIG. 13 shows dissolution profile of crystalline Abiraterone acetate, physical mixture, Zytiga and complex Abiraterone acetate in FeSSIF medium.

Dissolution of crystalline Abiraterone acetate, physical mixture of the composition of the present disclosure, wet milled composition of the present disclosure and complex Abiraterone acetate formulation of the present disclosure was measured by UV-VIS spectroscopy at 37° C. 10 mg Abiraterone acetate equivalent samples were dispersed in 20 mL FaSSIF and FeSSIF media and were filtered by 100 nm (crystalline Abiraterone acetate, Zytiga and the physical mixture) or a 20 nm (Abiraterone complex) disposable syringe filter. The active content in the filtrate was measured by UV-Vis spectrophotometry (FIG. 12 and FIG. 13).

Stability of the Solid Form

Figure 14:
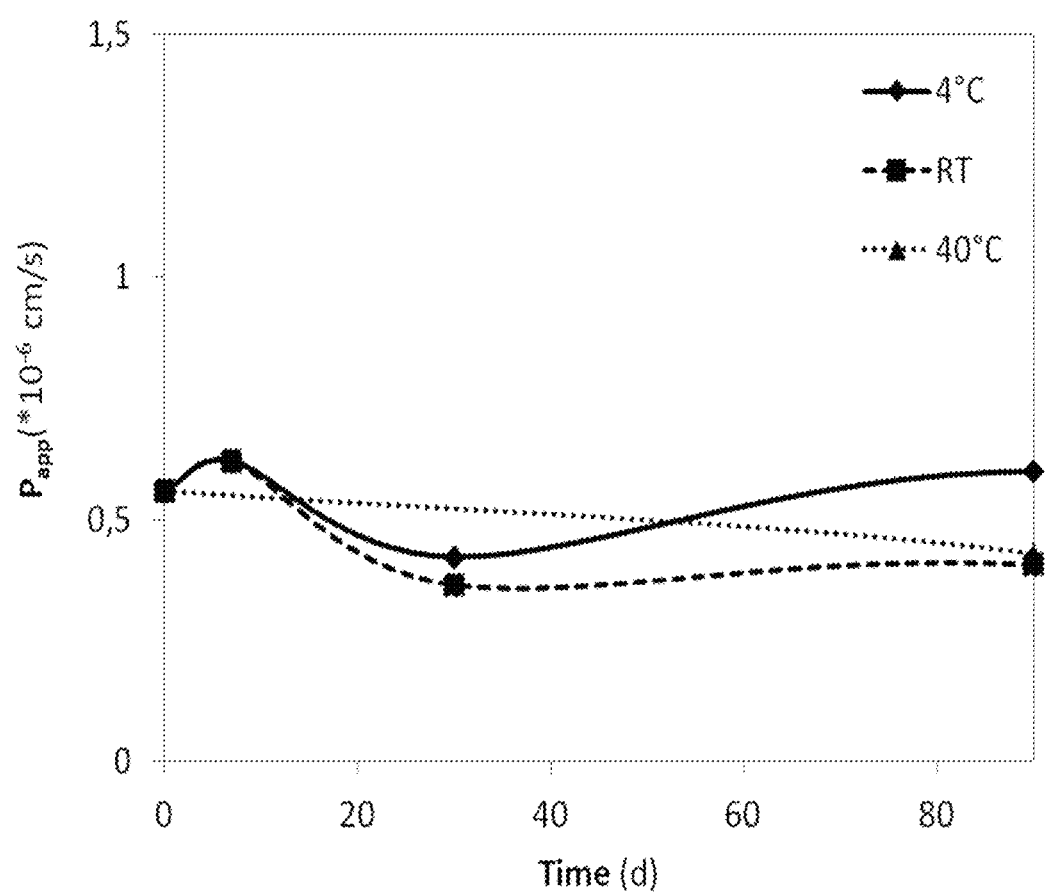
FIG. 14 shows the stability of the solid form detected as the PAMPA permeability measured after redispersion in distilled water after storage at different conditions.

PAMPA permeability of the solid complex is measured after storage at different conditions. 3 month storage at 4° C., RT or 40° C. 75% relative humidity showed no significant decrease in the measured PAMPA permeability under any of the conditions tested (FIG. 14).

Structural Analysis

Figure 15:
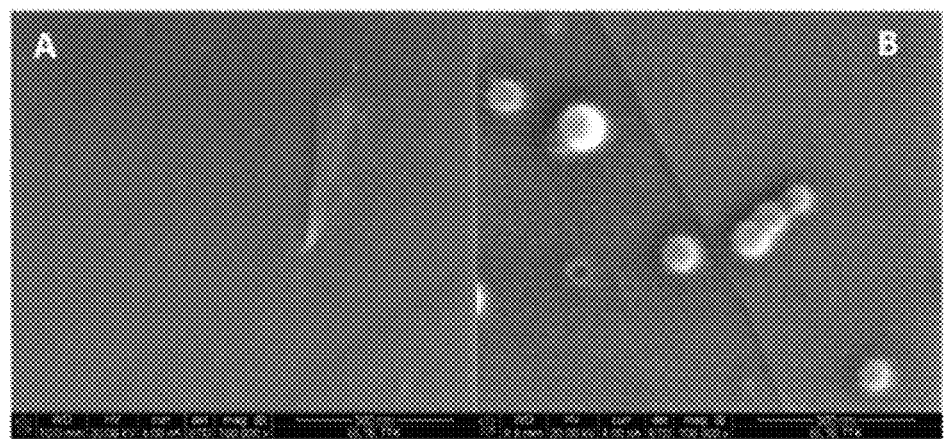
FIG. 15 shows scanning electron microscope (SEM) images about the complexes of Abiraterone acetate according to the present disclosure (B: the complex of the present disclosure containing Abiraterone acetate, polyvinylcaprolactam-polyvinyl acetate-polyethylene-glycol graft copolymer (Soluplus) and sodium deoxycholate; D: the complex of the present disclosure containing Abiraterone acetate, polyvinylcaprolactam-polyvinyl acetate-polyethylene-glycol graft copolymer (Soluplus), caprylic/capric triglyceride (Miglyol 812 N) and sodium deoxycholate and poloxamer (poloxamer 407)) and the placebo samples prepared in the absence of Abiraterone acetate (A and C).

Morphology of complex Abiraterone acetate formulation was investigated using PEI Quanta 3D scanning electron microscope. The morphology of the complex of the present disclosure was compared to the placebo samples (prepared in the absence of Abiraterone acetate), prepared as described above. Complexes of Abiraterone acetate of the present disclosure consists of spherical particles (FIG. 15 B). In the lack of the active compound, the complexing agent(s) and pharmaceutically acceptable excipient(s) do not form spherical particles (FIG. 15A).

Structural analysis was performed by using Bruker Vertex 70 FT-IR spectrometer with Bruker Platinum diamond ATR unit and HORIBA JobinYvon LabRAM HR UV-VIS-NIR equipped with Olympus BXFM free-space microscope using a 785 nm (NIR) diode laser.

Figure 16:
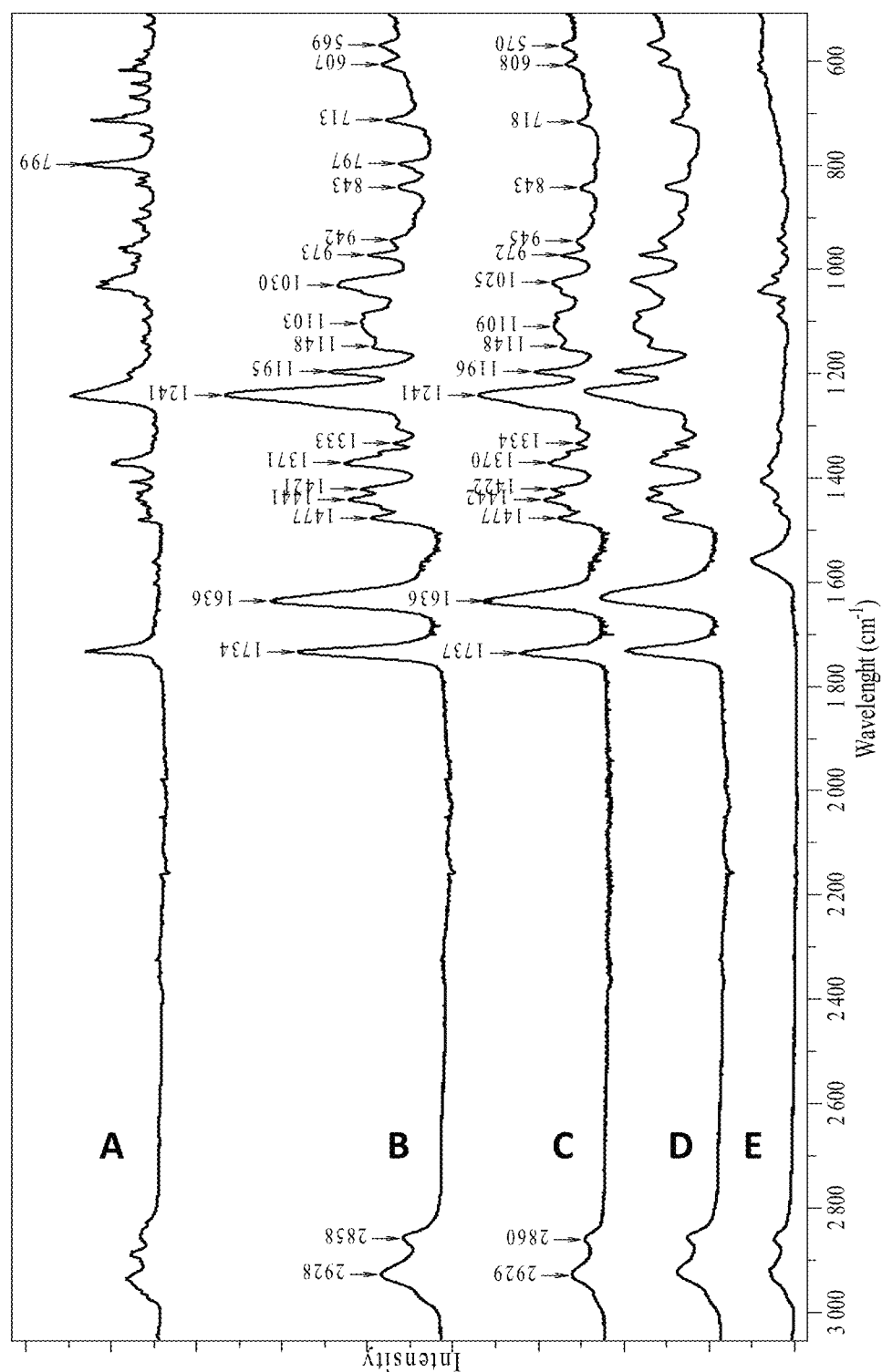
FIG. 16 shows ATR spectra of crystalline Abiraterone acetate (A), complex Abiraterone acetate (B), placebo sample (C), polyvinylcaprolactam-polyvinyl acetate-polyethylene-glycol graft copolymer (Soluplus) (D) and sodium deoxycholate (E)

In an embodiment, said complex is characterized by infrared (ATR) spectrum having main/characteristic absorption peaks at least at 569 cm$^{-1}$, 607 cm$^{-1}$, 713 cm$^{-1}$, 797 cm$^{-1}$, 843 cm$^{-1}$, 942 cm$^{-1}$, 973 cm$^{-1}$, 1030 cm$^{-1}$, 1103 cm$^{-1}$, 1148 cm$^{-1}$, 1195 cm$^{-1}$, 1241 cm$^{-1}$, 1333 cm$^{-1}$, 1371 cm$^{-1}$, 1421 cm$^{-1}$, 1441 cm$^{-1}$, 1477 cm$^{-1}$, 1336 cm$^{-1}$, 1734 cm$^{-1}$, 2858 cm$^{-1}$, 2928 cm$^{-1}$ characteristic absorption peaks (FIG. 16).

In an embodiment, said complex is characterized by infrared (ATR) spectrum having main/characteristic absorption peaks at least at 713 cm$^{-1}$, 1030 cm$^{-1}$, 1103 cm$^{-1}$ 1734 cm$^{-1}$, characteristic absorption peaks.

Figure 17:
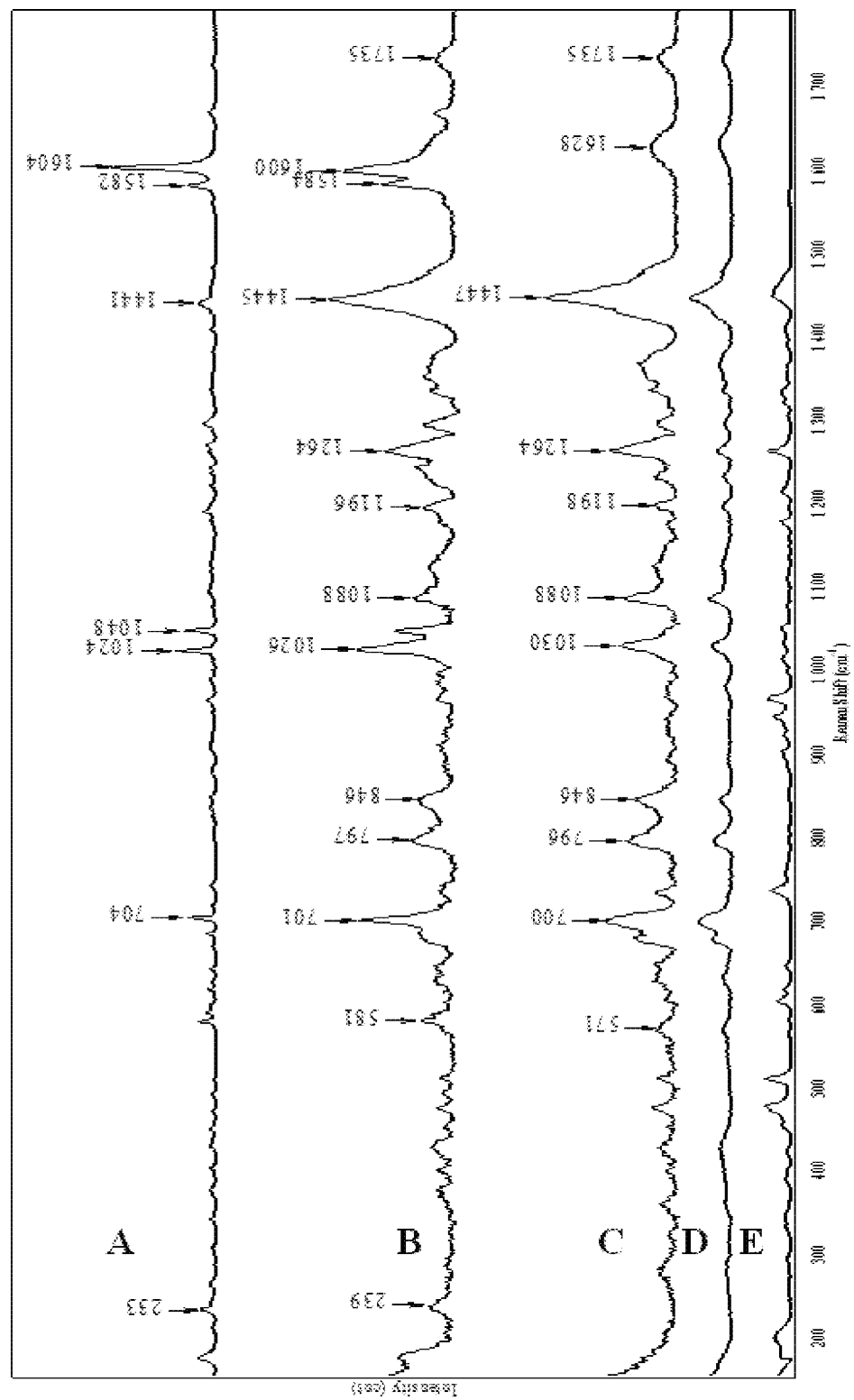
FIG. 17 shows Raman spectra of crystalline Abiraterone acetate (A), complex Abiraterone acetate (B), placebo sample (C), polyvinylcaprolactam-polyvinyl acetate-polyethylene-glycol graft copolymer (Soluplus) (D) and sodium deoxycholate (E)

In an embodiment, said complex is further characterized by Raman spectrum having main/characteristic absorption peaks at 239 cm$^{-1}$, 581 cm$^{-1}$, 701 cm$^{-1}$, 797 cm$^{-1}$, 846 cm$^{-1}$, 1026 cm$^{-1}$, 1088 cm$^{-1}$, 1196 cm$^{-1}$, 1264 cm$^{-1}$, 1445 cm$^{-1}$, 1584 cm$^{-1}$, 1600 cm$^{-1}$, 1735 cm$^{-1}$ (FIG. 17).

In an embodiment, said complex is further characterized by Raman spectrum having main/characteristic absorption peaks at 581 cm$^{-1}$, 1026 cm$^{-1}$, and 1445 cm$^{-1}$.

Figure 18:
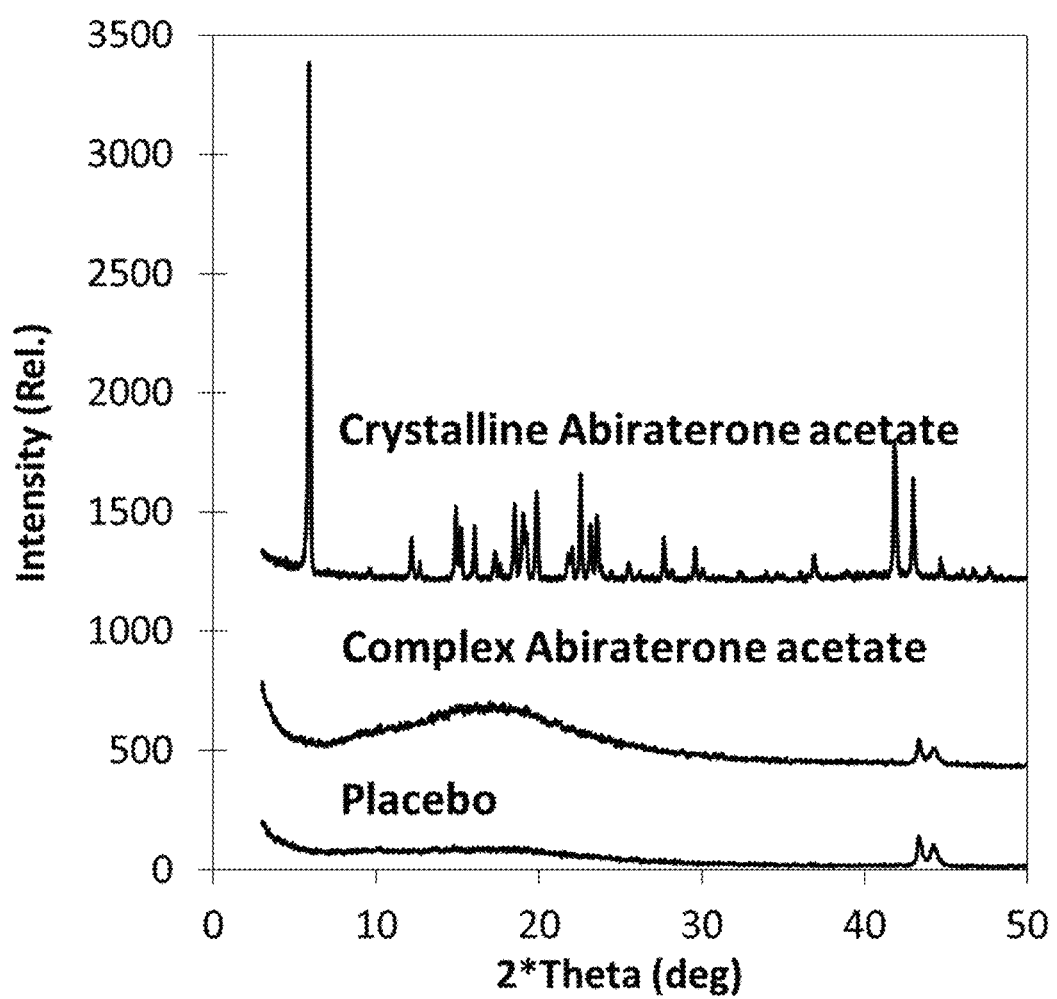
FIG. 18 shows powder X-ray diffractograms of crystalline Abiraterone acetate, place sample and complex Abiraterone acetate formulation.

The structure of the complex Abiraterone acetate of the present disclosure was investigated by powder X-ray diffraction (XRD) analysis (Philips PW1050/1870 RTG powder-diffractometer). The measurements showed that the complex Abiraterone acetate composition was XRD amorphous (see in FIG. 18). Characteristic reflections on the diffractogram of complex Abiraterone acetate and placebo sample are be attributed to sample holder.

Pharmaceutical Formulation 50 mg dose strength powder in a bottle (PIB) formulation of complex Abiraterone acetate of the present disclosure was prepared. Following production parameters were used for the manufacturing process:

Solvent 1: Tetrahydrofuran
$C_{Abiraterone\ acetate}$: 10 mg/mL
$C_{Soluplus®}$: 40 mg/mL
Solvent 2: Purified water
$C_{Sodium\ deoxycholate}$: 3.5 mg/mL
Flow rate$_{Solution\ 1}$: 10.0 mL/min
Flow rate$_{Solution\ 2}$: 40.0 mL/min
Temperature: 30° C.
Filling volume: 25 mL
Freezing time: 30 min in dry-ice/Acetone bath at least
Freeze-drying time: 36 h at least Abiraterone acetate content of the produced colloid was investigated right after the production and after filtration with 0.45 µm pore size filter. The active content of the colloid solution was 2.007 mg/mL, while the Abiraterone acetate content of the filtrate was found to be 2.026 mg/mL. The nominal active content of the solution mixture is 2.000 mg/mL.

Determination of Mass Uniformity of PiB Formulation:

25 mL aliquots of produced solution mixture were filled into 200 mL amber glass pharmaceutical bottles. The weight of the PiB formulation was checked after the freeze-drying process. The average mass of the freeze-dried powders in the bottles was 0.2773 mg±0.0015 mg.

Determination of Content Uniformity of PiB Formulation:

Content uniformity of the freeze-dried PiB formulations was investigated. The freeze-dried powder was dissolved in methanol. The Abiraterone acetate content was measured by HPLC method. Each samples tested met AV NMT 15 criterion.

Determination of Stability of PiB Formulation in Solid and Reconstituted Solution:

Abiraterone acetate complex PiB formulations were reconstituted with 50 mL purified water right after the production and 2 weeks storage at 40° C. The stability of reconstituted colloid solutions were monitored in time determining the active content of the colloid solution after filtration with 0.45 µm pore size filter. The Abiraterone acetate contents of the filtrate were in a good agreement right after the production and 2 weeks storage. Both reconstitutions resulted in homogenous opalescent colloid solutions which were practically free of visible particles.

The reconstituted colloid solution was ready for administration within 10 minutes. The reconstituted solution was stable for at least 4 hour at room temperature.

Determination of pH of Reconstituted PiB Formulations:

pH of the reconstituted PiB formulations of complex Abiraterone acetate of the present disclosure was investigated. The pH of each reconstituted solution was within the pH range recommended by the ICH guidelines for the products intended for oral administration (Table 4).

TABLE 4

| pH of reconstituted solutions | |
|---|---|
|  | pH |
| Right after the production |  |
| Reconstitution with 50 mL purified water | 7.35 |
| After 2 months storage |  |
| Reconstitution with 50 mL purified water | 7.40 |

Determination of Water Content of PiB Formulation:

Karl Fischer titration was used to determine the water content of the PiB formulations of complex Abiraterone acetate of the present disclosure right after the production (Table 5).

TABLE 5

| Water content of PiB formulations right after the production | | | |
|---|---|---|---|
| Bottle ID | Water content (%) | Average | SD |
| U0161 | 1.85 | | |
| U0161 | 1.74 | 1.84 | 0.10 |
| U0161 | 1.93 | | |

Measured at RH = 75%

The water content of the formulation met the acceptance criteria specified in the relevant ICH guidelines in each case.

Reconstitution and Administration for 50 mg Dose:

Reconstitution of the PiB formulations of complex Abiraterone acetate of the present disclosure using 50 mL Ph·Eur water yielded an opalescent solution within 10 minutes. This solution had to be administered orally. Another 190 mL of Ph·Eur water should be added to the bottle making the total of orally administered volume 240 mL.

Reconstitution and Administration for 100 mg Dose:

Reconstitution of the PiB formulations of complex Abiraterone acetate of the present disclosure using 50 mL of Ph·Eur water yielded an opalescent solution. This liquid had to be administered orally. Another 70 mL of Ph·Eur water should be added to the bottle and administered orally. The administration should be repeated using a second bottle of 50 mg strength PiB formulation. The total of orally administered volume will be 240 mL.

Reconstitution and Administration for 200 mg Dose:

Reconstitution of the PiB formulations of complex Abiraterone acetate of the present disclosure using 50 mL of Ph·Eur water yielded an opalescent solution. This liquid has to be administered orally. Another 10 mL of Ph·Eur water should be added to the bottle and administered orally. The administration should be repeated four times using another three bottles of 50 mg strength PiB formulation. The total of orally administered volume will be 240 mL.

The reconstitution of the PiB formulations of the complex Abiraterone acetate of the present disclosure was tested. Different amount of Ph·Eur water was added to the PiB formulations in order to reconstitute the freeze-dried powder. The Abiraterone acetate content of the reconstituted colloid solutions was measured. Then the bottles were rinsed once adding 10 mL of Ph·Eur water. The Abiraterone acetate content of rising liquid was also measured. Finally the bottles were rinsed with methanol to dissolve completely the remaining Abiraterone acetate. The Abiraterone acetate content was also determined in this case (Table 6). More than 98% of the Abiraterone acetate content was in the reconstituted volume. After 1 rising step less than 0.7% Abiraterone acetate remained in the bottles.

TABLE 6

Abiraterone acetate content of the PIB formulations after reconstitution

| Bottle ID: U0920 | $c_{Solution}$ (mg/mL) | Abiraterone acetate content (mg) |
|---|---|---|
| $V_{Ph.Eur\ water}$ = 50 mL | 1.0404 | 52.02 |
| Rinsing with $V_{Ph.Eur\ water}$ = 10 mL | 0.0747 | 0.75 |
| Rinsing with $V_{Methanol}$ = 10 mL | 0.0390 | 0.39 |
| Total | | 53.16 |

In-Vivo Pharmacokinetics

In-Vivo PK Test in Animals

Figure 19:
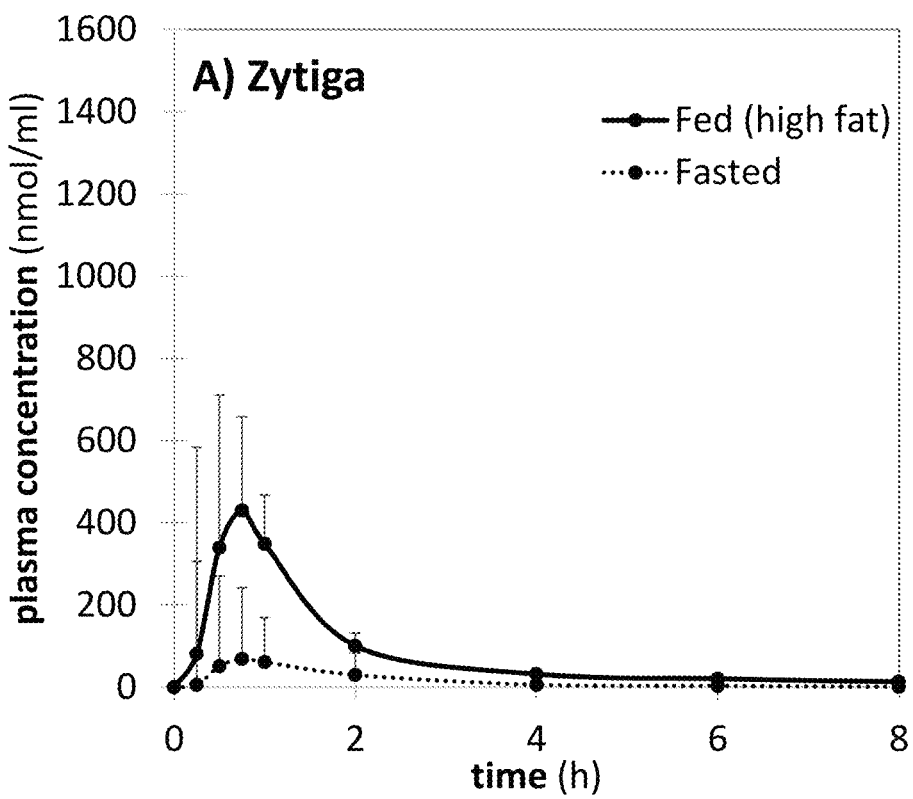
FIG. 19 shows the plasma Abiraterone concentrations following the oral administration of 50 mg Zytiga (A) and Complex Abiraterone acetate (B) according to the disclosure to beagle dogs (11-13 kg, n=4) in the fasted and in the fed conditions.
Figure 19:
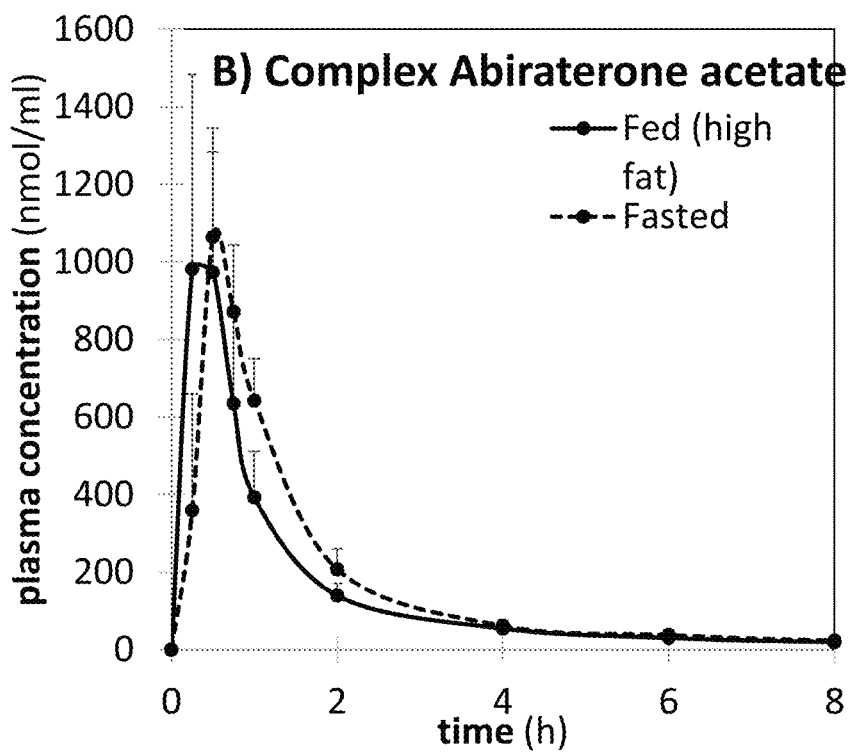

The administration of 50 mg Zytiga to beagle dogs in the fasted and in the fed (high fat) state absorption was rapid in both cases, however, plasma concentrations, $C_{max}$ and $AUC_{inf}$ values were over 5-fold lower in the fasted state than in the fed (high fat) state (FIG. 19 A). Following oral administration of the complex Abiraterone acetate formula to fasted and fed (high fat) beagle dogs the maximal plasma Abiraterone concentrations were detected at 0.5 hour indicating immediate absorption of the Abiraterone acetate from the Complex Abiraterone acetate formulation of the present disclosure. No significant differences were observed in the plasma concentrations when the compound was administered in the fasted or in the fed (high fat) state (FIG. 19 B). $AUC_{inf}$ and $C_{max}$ values calculated from the curves showed significantly higher exposure for the Complex Abiraterone acetate formula than for Zytiga both in the fasted and in the fed state along with total elimination of the positive food effect Zytiga exhibits (Table 7).

TABLE 7 shows pharmacokinetic parameters following the oral administration of Zytiga of the Complex Abiraterone acetate formulation to beagle dogs. N = 4, dose: 50 mg.

| Test article | Feeding condition | $t_{max}$ (h) | $C_{max}$ (nmol/ml) | $AUC_{last}$ (h * nmol/ml) |
|---|---|---|---|---|
| Complex Abiraterone | Fasted | 0.50 ± 0 | 1064 ± 219 | 1575 ± 339 |
| Complex Abiraterone | High fat meal | 0.38 ± 0.13 | 1086 ± 433 | 1345 ± 435 |
| Zytiga | Fasted | 1.06 ± 0.54 | 76 ± 38 | 138 ± 75 |
| Zytiga | High fat meal | 0.81 ± 13 | 443 ± 215 | 773 ± 300 |

Pharmacokinetics in Healthy Man

Figure 20:
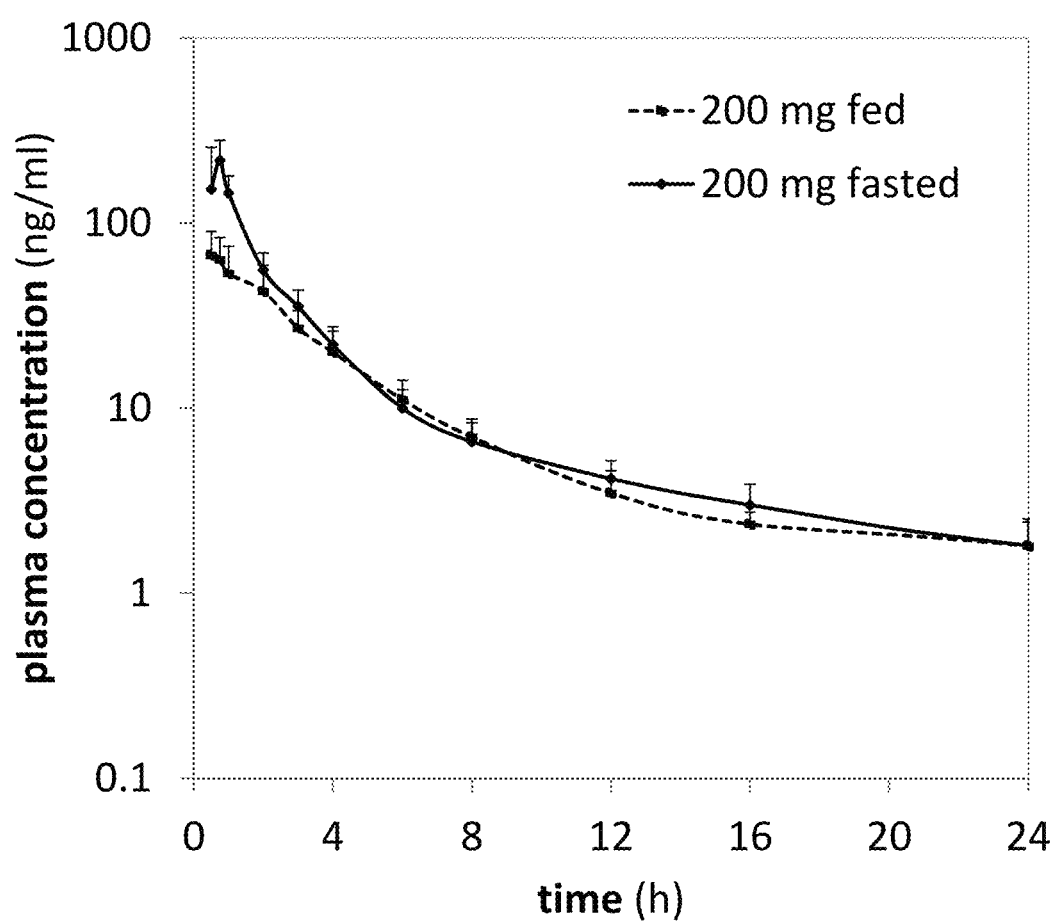
FIG. 20 shows plasma concentration of Abiraterone following the oral administration of 200 mg Complex Abiraterone acetate formula to 10 healthy male volunteers in the fasted and in the fed state.

Ten healthy male volunteers between the ages of 45 and 65 were enrolled in a clinical pharmacokinetic study where 200 mg of the Complex abiraterone formula was administered orally in the fasted and in the fed state. Maximal plasma abiraterone concentrations were detected at 0.5 hour indicating immediate absorption of the active ingredient from the formula. No significant increase was observed in the plasma concentrations in the fed state when compared to the fasted state, actually, there plasma concentration were lower in the fed state at early time points, while were practically identical after the 4 hour time point (FIG. 20). $AUC_{inf}$ and $C_{max}$ values calculated from the curves and variability of exposure and food effect was calculated form these pharmacokinetic parameters and compared to published clinical pharmacokinetic data for 1000 mg Zytiga (Table 8). AUC in the fasted state for the 200 mg dose of the Complex Abiraterone Acetate was 80% of the 1000 mg dose for Zytiga, therefore, significant dose reduction is possible using the Complex Abiraterone Acetate formula. Also, the very large positive food effect was eliminated which shows that the requirement for Zytiga to be taken for an empty stomach was eliminated. The variability of exposure was also significantly reduced. The elimination half life was identical to data published for Zytiga (EMEA Assessment Report For Zytiga (abiraterone)).

TABLE 8 shows pharmacokinetic parameters following the oral administration of 1000 mg Zytiga (*EMEA Assessment Report For Zytiga (abiraterone)*, Acharya et al., 2012 and Attard et al., 2008.) or 200 mg Complex Abiraterone acetate formulation to 10 healthy male volunteers in the fasted and in the fed state.

| | ZYTIGA FASTED* | COMPLEX ABIRATERONE, FASTED | COMPLEX ABIRATERONE, FED |
|---|---|---|---|
| Dose (mg) | 1000 | 200 | 200 |
| $AUC_{last}$ (ng * h/ml) (% of 1000 mg Zytiga) | 503 (100) | 399 (80) | 295 (59) |
| $C_{max}$ (ng/ml) | 93.5 | 206 | 72 |
| Variability ($AUC_{last}$ CV %) | 0.5 | 0.3 | 0.2 |
| Variability (max/min $AUC_{last}$) | 9 | 2.3 | 2.2 |
| Food effect (fed/fasted $AUC_{last}$) | 5 | | 0.74 |
| $t_{1/2}$ (h) | 16 | 15 | 13 |

Enteric Coated Tablet Containing Complex Abiraterone Acetate

Freeze dried complex Abiraterone acetate formulation of the present disclosure was dry granulated via slugging or roll compaction in order to obtain powder with sufficient flowability. The particle size of the granulated complex Abiraterone acetate formulation was between 160-320 μm. The granulated complex Abiraterone acetate formulation was then blended with lactose-monohydrate, microcrystalline cellulose as fillers, crosscarmellose sodium as disintegrant and sodium-deoxycholate as absorption supporting agent (Table 9).

TABLE 9 shows Composition of the complex Abiraterone tablets.
Composition of complex Abiraterone acetate granulation

| | | |
|---|---|---|
| Granulated complex Abiraterone | active ingredient | 31.32 w/w % |
| Lactose-monohydrate (Flowlac 100) | filler | 31.32 w/w % |
| Microcrystalline-cellulose (Vivapur 101) | filler | 15.66 w/w % |
| Croscarmellose sodium | disintegrant | 14.99 w/w % |
| Sodium-deoxycholate | absorption supporting agent | 6.71 w/w % |

The powder mixture containing granulated complex Abiraterone acetate formulation of the present disclosure was compressed into tablets with 50 mg dose strength. Disintegration time of the tablets containing complex Abiraterone acetate formulation in simulated intestinal fluid was less than 5 minutes. The cores of tablets containing complex Abiraterone acetate formulation were coated with anionic copolymer based on methacrylic acid and ethyl acrylate.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A stable solid complex with improved physicochemical characteristics and enhanced biological performance comprising a) Abiraterone acetate; b) at least one complexing agent which is a polyvinyl caprolactam-polyvinyl acetate-polyethylene glycol graft copolymer; and c) a pharmaceutically acceptable excipient which is sodium deoxycholate; wherein said complex is not obtained via a milling process, by high pressure homogenization process, encapsulation process or solid dispersion process; said complex has a particle size less than 600 nm, and possesses one or more among the following features:

a) it is instantaneously redispersible in physiological relevant media;
    b) it has increased dissolution rate compared to Zytiga (containing 250 mg of abiraterone acetate per tablet);
    c) it is stable in solid form and in colloid solution and/or dispersion;
    d) its apparent solubility in water is of at least 0.6 mg/mL;
    e) it has a permeability of $0.5 \times 10^{-6}$ cm/s in a parallel artificial membrane permeability assay (PAMPA) when dispersed in distilled water, which does not decrease in time at least for 3 months;
    f) exhibits no positive food effect (fed/fasted ration is under 1.25) which allows significant dose reduction and the abandoning of the requirement of taking the drug on an empty stomach; and
    g) the variability of exposure is significantly reduced when compared to Zytiga, said process comprising the step of mixing a solution of the active agent and at least one complexing agent and optionally one or more pharmaceutically acceptable excipient in a pharmaceutically acceptable solvent with an aqueous solution containing optionally least one pharmaceutically acceptable excipient.

2. The process as recited in claim 1, wherein said process is performed in a continuous flow instrument.

3. The process as recited in claim 2, wherein said continuous flow instrument is a microfluidic flow instrument.

4. The process as recited in claim 1, wherein said pharmaceutically acceptable solvent is chosen from water, methanol, ethanol, isopropanol, n-propanol, acetone, acetonitrile, dimethyl-sulfoxide, tetrahydrofuran, or combinations thereof.

5. The process as recited in claim 4, wherein said pharmaceutically acceptable solvent is a combination of water and tetrahydrofuran.

6. The process as recited in claim 1, wherein said solvents are miscible with each other and the aqueous solvent comprises 0.1 to 99.9% weight of the final solution.

* * * * *